United States Patent
Quinones-Mateu et al.

(10) Patent No.: US 10,144,976 B2
(45) Date of Patent: Dec. 4, 2018

(54) HIV-1 GENOTYPING AND CORECEPTOR TROPISM ASSAY

(71) Applicant: Case Western Reserve University, Cleveland, OH (US)

(72) Inventors: Miguel E. Quinones-Mateu, Rocky River, OH (US); Eric J. Arts, Cleveland Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 545 days.

(21) Appl. No.: 14/540,774

(22) Filed: Nov. 13, 2014

(65) Prior Publication Data

US 2015/0337399 A1    Nov. 26, 2015

Related U.S. Application Data

(60) Provisional application No. 62/002,025, filed on May 22, 2014.

(51) Int. Cl.
   *C12P 19/34* (2006.01)
   *C12Q 1/70* (2006.01)

(52) U.S. Cl.
   CPC .............. *C12Q 1/703* (2013.01); *C12Q 1/70* (2013.01); *C12Q 2600/106* (2013.01); *C12Q 2600/156* (2013.01); *C12Q 2600/158* (2013.01)

(58) Field of Classification Search
   USPC ................................................ 435/6.12, 91.2
   See application file for complete search history.

(56) References Cited

U.S. PATENT DOCUMENTS

| | | | |
|---|---|---|---|
| 6,081,786 A | 6/2000 | Barry et al. | |
| 6,188,988 B1 | 2/2001 | Barry et al. | |
| 6,489,098 B1 | 12/2002 | Petropoulos et al. | |
| 6,869,759 B1 | 3/2005 | Parkin et al. | |
| 7,138,231 B2 | 11/2006 | Parkin et al. | |
| 7,186,506 B1 | 3/2007 | Parkin et al. | |
| 7,206,699 B2 | 4/2007 | Larder et al. | |
| 7,235,387 B2 | 6/2007 | Larder et al. | |
| 7,553,618 B2 | 6/2009 | Parkin et al. | |
| 7,847,087 B2 | 12/2010 | Huong et al. | |
| 7,888,034 B2 | 2/2011 | Simen et al. | |
| 8,344,123 B2 * | 1/2013 | Simen .................... | C12Q 1/703 435/6.12 |
| 8,617,816 B2 * | 12/2013 | Simen .................... | C12Q 1/686 435/6.12 |
| 2008/0293038 A1 | 11/2008 | Parkin et al. | |
| 2010/0136516 A1 * | 6/2010 | Simen .................... | C12Q 1/703 435/5 |
| 2011/0020831 A1 | 1/2011 | Verhofstede et al. | |
| 2012/0244523 A1 | 9/2012 | St. John et al. | |
| 2012/0322665 A1 * | 12/2012 | St. John ................ | C12Q 1/703 506/2 |

OTHER PUBLICATIONS

US 8,501,409, 08/2013, Simen et al. (withdrawn)

* cited by examiner

*Primary Examiner* — Kenneth R Horlick
(74) *Attorney, Agent, or Firm* — Tarolli, Sundheim, Covell & Tummino LLP

(57) ABSTRACT

A method for detecting low frequency occurrence of one or more HIV sequence variants associated with drug resistance and HIV tropism includes generating a plurality of cDNA species from a plurality of RNA molecules in an HIV sample population, amplifying a plurality of first amplicons and second amplicons from the cDNA species, wherein the first amplicons are amplified using first pairs of primers that amplify a HIV genomic region of the cDNA species encoding the Gag proteins p2, p7, p1 and p6, and the protease, reverse transcriptase, and integrase enzymes and the second amplicons are amplified using second pairs of primers that amplify a HIV genomic encoding region of the cDNA species encoding the env-C2V3 region; determining the nucleic acid sequence compositions of the amplified first amplicons second amplicons; identifying variants in the determined sequence by comparing the determined nucleic sequence to a guide sequence; and correlating the determined variants with variants of HIV drug resistance and HIV tropism.

23 Claims, 8 Drawing Sheets
Specification includes a Sequence Listing.

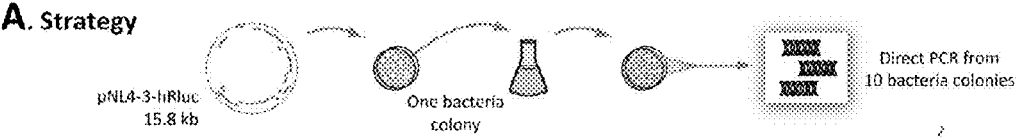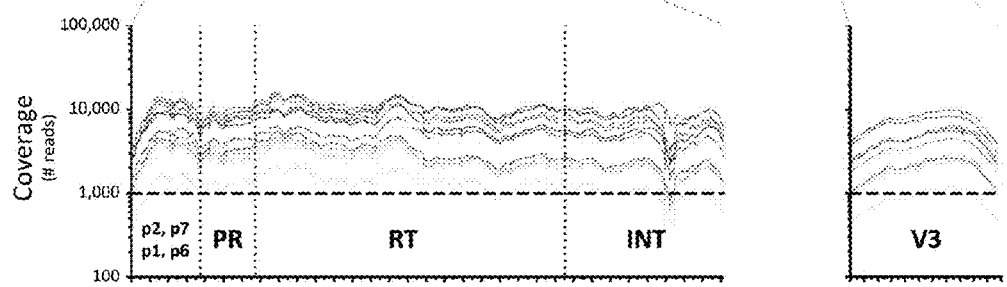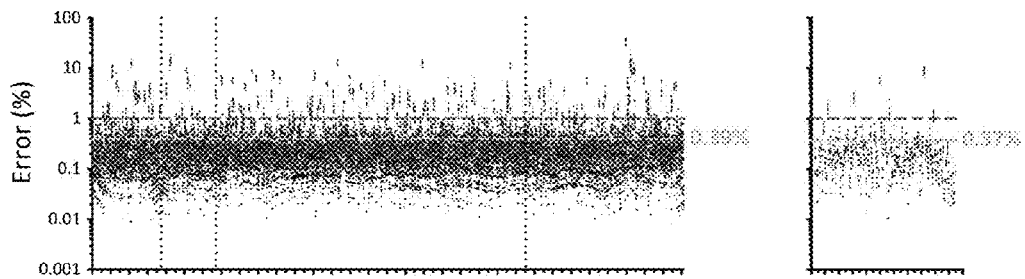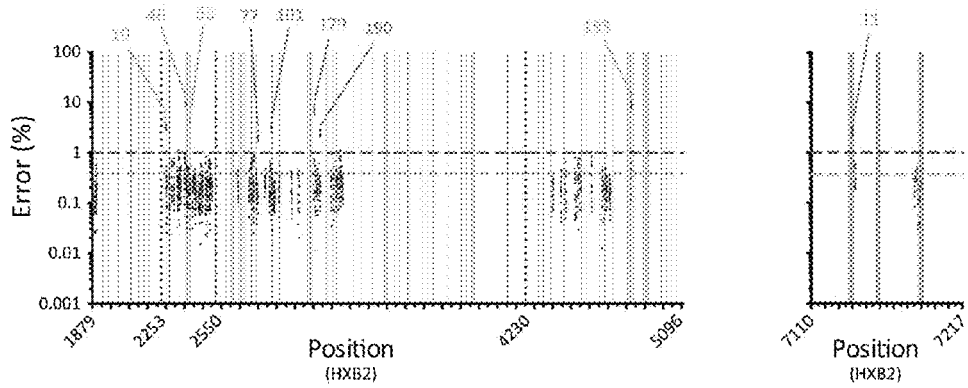
Figs. 2A-D

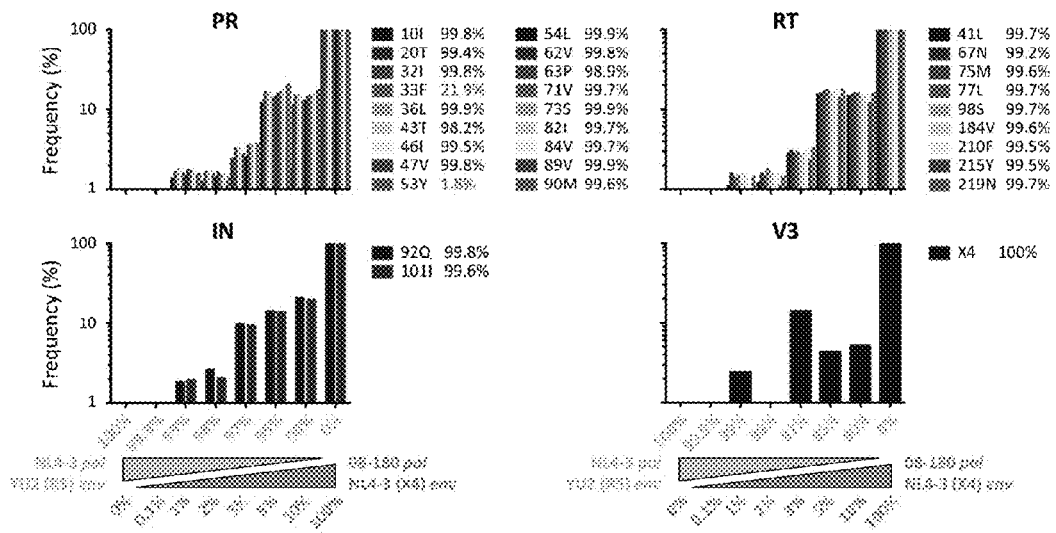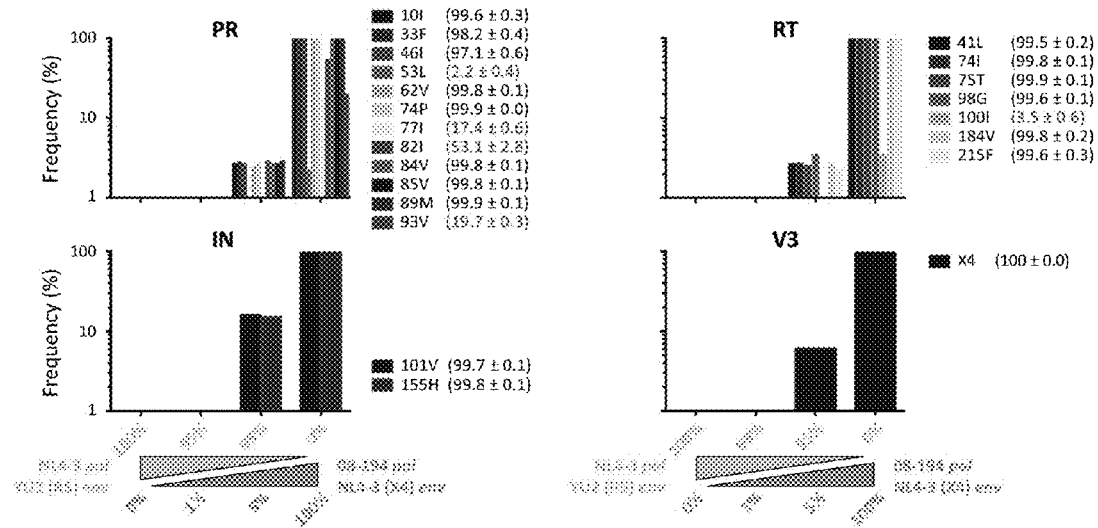
Figs. 3A-B

A. Experiment Design
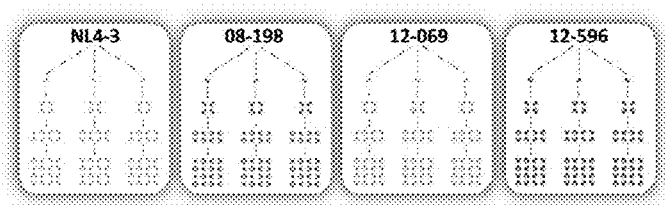
B. Genetic Diversity
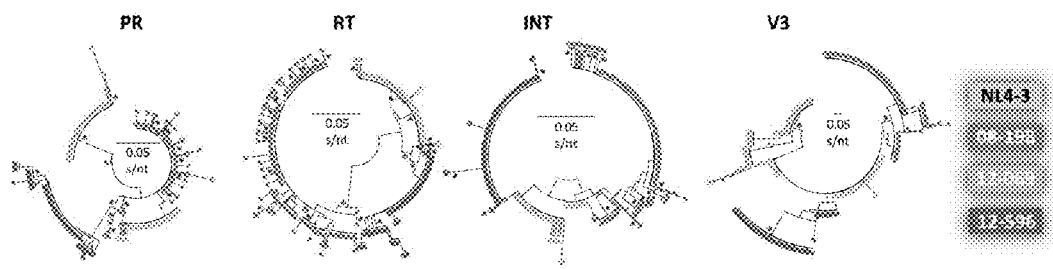
C. Reproducibility (nt)
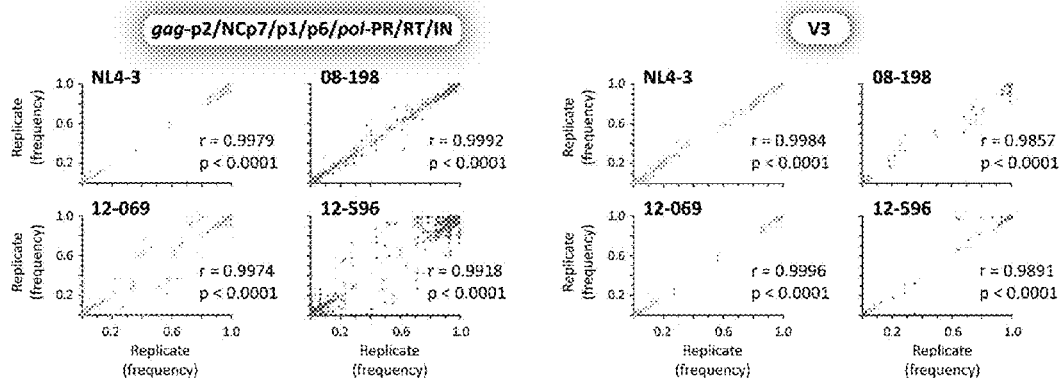
Figs. 4A-C

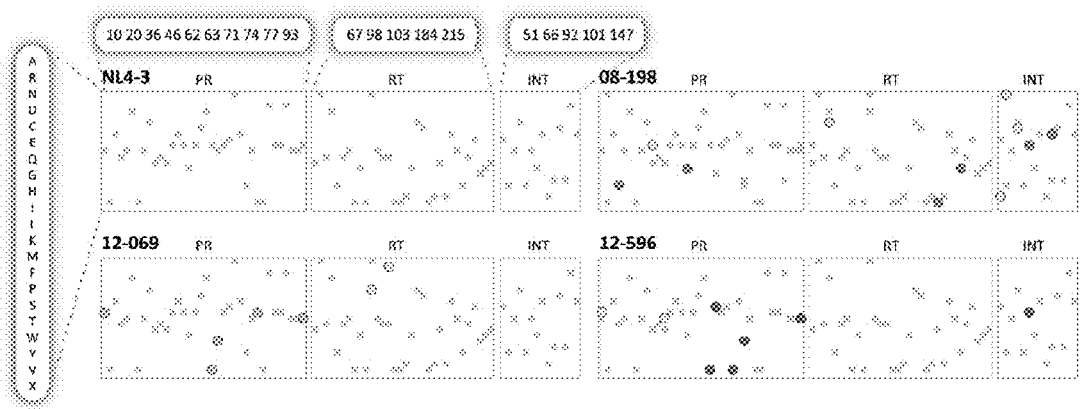
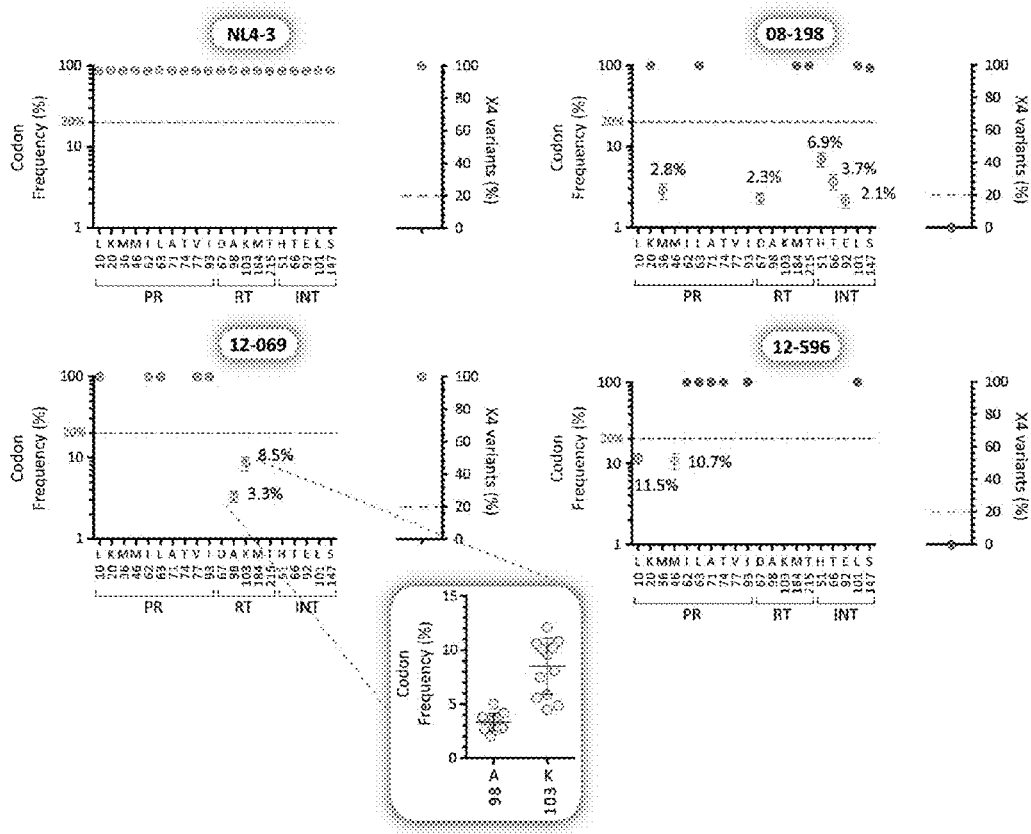
Figs. 4D-E

A. Correlation of DEEPGEN with population sequencing
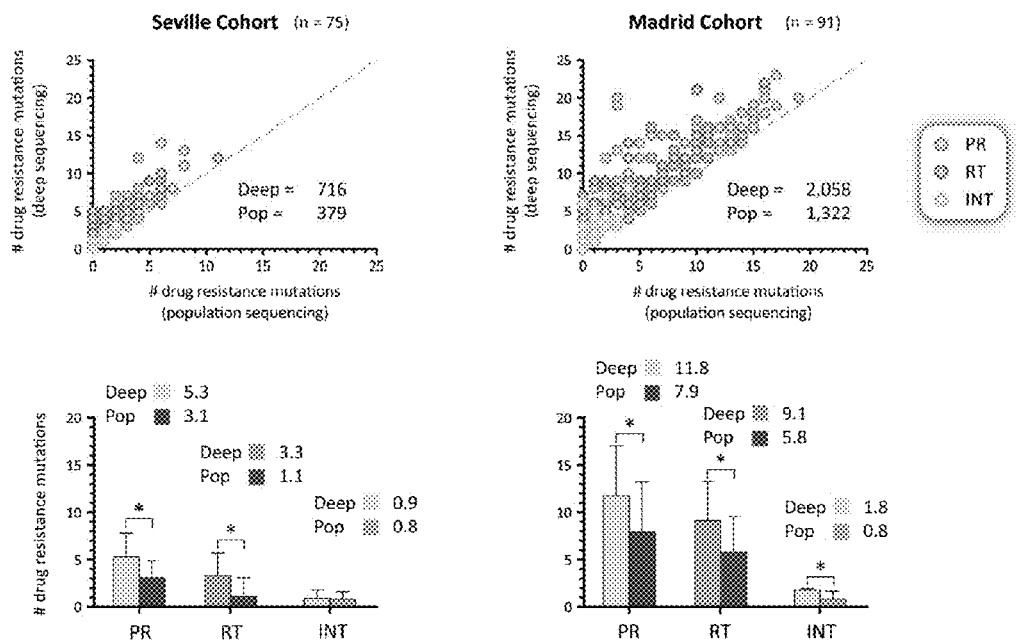
B. Correlation of DEEPGEN with other HIV-1 tropism tests
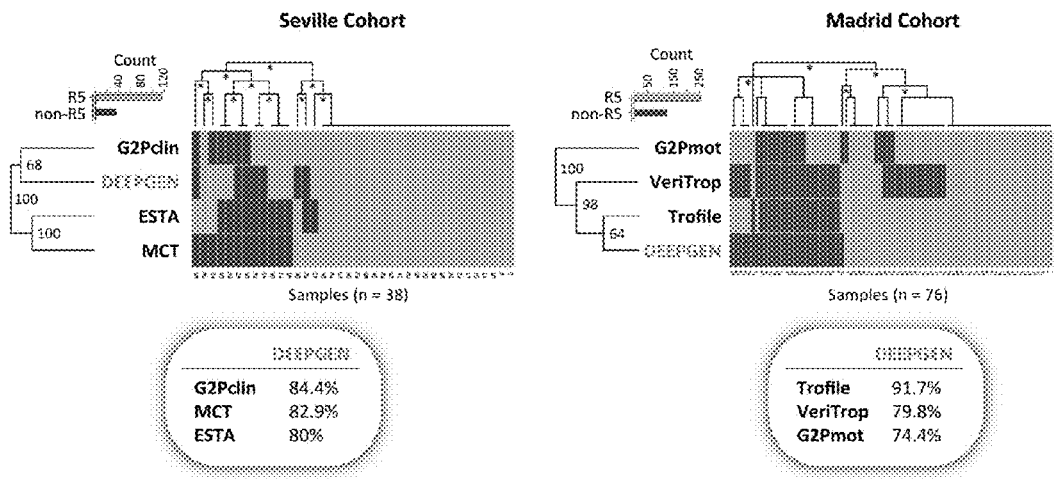
Figs. 5A-B

SEQUENCE LISTING

<160> NUMBER OF SEQ ID NOS: 2

<210> SEQ ID NO 1
<211> LENGTH: 41
<212> TYPE: DNA
<213> ORGANISM: Artificial Sequence
<220> FEATURE:
<223> OTHER INFORMATION: Synthetic Primers

<400> SEQUENCE: 1
ccactacgcc tccgctttcc tctctatggg cagtcggtga t					41

<210> SEQ ID NO 2
<211> LENGTH: 43
<212> TYPE: DNA

```
<213> ORGANISM: Artificial Sequence
<220> FEATURE:
<223> OTHER INFORMATION: Synthetic Primers

<400> SEQUENCE: 2
atcaccgact gcccatagag aggaaagcgg aggcgtagtg gtt                           43
```

HIV-1 GENOTYPING AND CORECEPTOR TROPISM ASSAY

RELATED APPLICATION

This application claims priority from U.S. Provisional Application No. 62/002,025, filed May 22, 2014, the subject matter of which is incorporated herein by reference in its entirety.

GOVERNMENT FUNDING

This invention was made with government support under Grant No. AI049170 awarded by The National Institutes of Health, National Institute of Allergy and Infectious Diseases, and the State of Ohio. The United States government has certain rights in the invention.

BACKGROUND

The Human Immunodeficiency Virus (HIV) continues to be a major problem worldwide, even though a plethora of compounds have been approved for treatment. Due to the error-prone nature of viral reverse transcriptase and the high viral turnover ($t_{1/2}$=1-3 days), the HIV genome mutates very rapidly. For example, reverse transcriptase is estimated to generate, on average, one mutation per replication of the 9.7 Kb genome that does not dramatically affect the ability of the virus to propagate. This leads to the formation of quasi-species, where many different mutants exist in a dynamic relationship.

To date, twenty-nine individual antiretroviral drugs from six drug classes have been approved by the U.S. Food and Drug Administration (FDA) to be used in the treatment of HIV-1 infection, including protease (PI), nucleoside/nucleotide reverse transcriptase (NRTI), non-nucleoside reverse transcriptase (NNRTI), integrase (INI), fusion (FI), and entry (EI), inhibitors. HIV-1 resistance to PI, NRTI, NNRTI, and INI can be determined using (i) indirect methods based on detection of specific amino acid substitutions (due to underlying nucleotide mutations) in the respective coding regions previously associated with resistance to specific antiretroviral drugs (i.e., genotyping), (ii) more direct methods that test the ability of a patient-derived virus to replicate in the presence of antiretroviral drugs in a cell-based assay (i.e., phenotyping), or (iii) a combination of both approaches that takes advantage of a large database to infer the level of HIV-1 drug resistance based on genotyping and its relationship with matched phenotypic data. Similarly, since treatment with CCR5 antagonists requires the prior knowledge of the HIV-1 coreceptor tropism in the patient, i.e., CCR5- or CXCR4-tropic viruses (R5 and X4, respectively), dual tropic (R5/X4), or a mixture of both R5 and X4 viruses, a multitude of phenotypic and genotypic approaches to determine HIV-1 coreceptor tropism have been developed. Phenotypic assays to determine HIV-1 drug resistance or tropism usually involve the generation of patient-derived pol- or env-recombinant viruses, respectively, to quantify their ability to infect susceptible cell lines expressing the appropriate HIV-1 receptors and coreceptors or, in the case of HIV-1 tropism, may also be based on the quantification of cell-to-cell fusion events. Whereas, genotypic HIV-1 tropism tests take advantage of the properties of specific regions in the env gene as determinants of CCR5 or CXCR4 tropism, mainly the V3 region of the gp120, and their interpretation based on a series of bioinformatic methods to infer the ability of HIV-1 to use any or both coreceptors to enter host cells.

As expected, phenotypic (experimental) and genotypic (computational) approaches to determine HIV-1 drug resistance or HIV-1 coreceptor tropism have some disadvantages, including the longer turnaround time and higher cost of the phenotypic assays or the intrinsic predictive nature of the genotypic tests. Particular emphasis has been made on the limited sensitivity of genotypic HIV-1 tropism assays to detect minor non-R5 variants, and to a lesser extent on the ability of genotypic HIV-1 drug resistance tests to detect minority drug resistant variants. In the case of HIV-1 drug resistance, the vast amount of information accumulated during the last two decades by correlating mutations with phenotypic data has led to the almost exclusive use of genotypic antiretroviral testing based on population (Sanger) sequencing to manage patients infected with HIV-1. In contrast, although several studies have shown significant concordance and similar predictive values, genotypic HIV-1 tropism assays based on population sequencing seem to be less sensitive and specific than phenotypic assays. Thus, a cell-based assay (Trofile, Monogram Biosciences) is currently the standard method to determine HIV-1 coreceptor tropism in the U.S., while genotypic HIV-1 tropism tests are largely used in Europe.

To date, all current commercial genotypic HIV-1 drug resistance assays are based on population sequencing, which can only detect minority variants present above 20% of the viral population. However, and although still uncertain, drug resistant HIV-1 minority variants (i.e., as low as 1% of the viral population) have been suggested to be clinically relevant as they have a high chance of being selected for under antiretroviral drug pressure.

SUMMARY

Embodiments described herein relate to methods of detecting low frequency occurrence of one or more HIV sequence variants (e.g., allelic variants, single nucleotide polymorphism variants, indel variants) associated with drug resistance and HIV tropism, such as non-R5 HIV variants. The method can detect sequence variants, which are present in a HIV sample in non-stoichiometric allele amounts, such as, for example, HIV variants present in less than 50%, less than 25%, less than 10%, less than 5% or less than 1% of the viral population.

In some embodiments, the method can include generating a plurality of cDNA species from a plurality of RNA molecules in an HIV sample population obtained from a subject. A plurality of first amplicons and second amplicons can be amplified from the cDNA species. The first amplicons are amplified using first pairs of primers that amplify a HIV genomic region of the cDNA species encoding the Gag proteins p2, p7, p1 and p6, and the protease, reverse transcriptase, and integrase enzymes. The second amplicons are amplified using second pairs of primers that amplify a HIV genomic encoding region of the cDNA species encoding env-C2V3 region. The nucleic acid sequence composition of the first amplicons and second amplicons can then be determined using next generation or deep sequencing methods, such as massively parallel signature sequencing (MPSS), polony sequencing, pyrosequencing, Illumina dye sequencing, SOLiD sequencing, nanopore sequencing, semiconductor sequencing (Ion Torrent), sequencing-by-ligation, sequencing-by-hybridization, RNA-Seq (Illumina), Digital Gene Expression (Helicos), Single Molecule Sequencing by Synthesis (SMSS) (Helicos), Clonal Single Molecule Array (Solexa), shotgun sequencing, and Maxim-Gilbert sequencing. A guide sequence with minimal divergence from the determined nucleic acid sequence composition can be selected for mapping variants of the determined nucleic acid compositions by comparing the determined nucleic acid sequence compositions to reference sequences. Variants occurring at least 1% in the determined nucleic acid sequence compositions are identified by comparing the determined nucleic sequence to the guide sequence. The determined variants are then correlated with variants of HIV drug resistance and HIV tropism.

In some embodiments, the first amplicons can include a first and second overlapping amplicon fragments corresponding to the genomic region encoding p2 to 5' region of reverse transcriptase enzyme and the genomic region encoding 3' region of reverse transcriptase enzyme to integrase enzyme.

In other embodiments, the variation associated with HIV tropism is known to be associated with the coreceptor, CCR5 and CXCR4.

In still other embodiments, the variation associated with HIV drug resistance is known to be associated with a particular drug class or drug. The HIV drug class can be selected from the group consisting of protease inhibitors, integrase inhibitors, nucleotide/nucleoside reverse transcriptase inhibitors, non-nucleoside reverse transcriptase inhibitors, and maturation inhibitors.

BRIEF DESCRIPTION OF THE DRAWINGS

FIGS. 2(A-D) illustrate a schematic drawing and plots showing an error rate determination for the HIV-1 genotyping and coreceptor tropism assay described herein. (A) The pNL4-3-hRluc plasmid containing the entire genome of the wild type HIV-1NL4-3 strain was transformed into bacteria and the gag-p2/NCp7/p1/p6/pol-PR/RT/IN and env-C2V3 fragments were PCR amplified and deep sequenced from ten individual colonies. Reads from each individual NL4-3 clone were independently mapped to the pNL4-3-hRluc reference sequence using Segminator II. (B) Coverage, i.e., number of reads per nucleotide position, for the ten NL4-3 clones. (C) Overall (point mutation, insertions, and deletions) error rate per nucleotide position calculated using a Phred Quality Score of 20. (D) Overall error rate in positions associated with drug resistance. Only codon changes with error rates above 1% are indicated, i.e., L10, M46, and F53 in the protease; F77, K101, V179, and G190 in the RT; G193 in the integrase; and amino acid 11 in the V3 region. Homopolymeric regions, defined as four or more identical consecutive nucleotides, are indicated as vertical bars.

FIGS. 3(A-B) illustrate graphs showing the ability of the HIV-1 genotyping and coreceptor tropism assay to detect drug resistance mutations (in the gag-p2/NCp7/p1/p6/pol-PR/RT/IN fragment) and non-R5 variants (in the env-V3 region) within mixtures of viral populations. (A) A gagp2/NCp7/p1/p6/pol-PR/RT/IN PCR product was obtained from an antiretroviral-experienced patient (08-180) and used to construct p2-INT recombinant viruses based on the yeast cloning method to maintain the HIV-1 quasispecies. This plasmid preparation contained the pol gene from the patient and the env gene from the CXCR4-tropic HIV-1NL4-3 strain, i.e., 08-180 pol/NL43-(X4)env. Plasmid NL4-3 pol/YU2(R5)env contains the genome of the wild-type HIV-1NL4-3 virus carrying the env gene from the R5 HIV-1YU2 virus. A series of plasmid mixtures were created by mixing 0.1%, 1%, 2%, 3%, 5% and 10% of the 08-180pol/NL43-(X4)env plasmid with the corresponding amount of the NL4-3pol/YU2(R5)env plasmid at a final concentration of 0.1 ng/ml. DNA from the entire plasmid mixtures, together with the two individual plasmids as controls (100%), was purified and deep sequenced as described in Materials and Methods. (B) Plasma containing a patient-derived multidrug resistant gag-p2/NCp7/p1/p6/pol-PR/RT/IN recombinant virus constructed using the X4 HIV-1NL4-3 backbone (08-194) and a wild-type HIV-1NL4-3 virus carrying the env gene from the R5 HIV-1YU2 virus were mixed at 0%, 1%, 5% and 100% of the 08-194 virus at a final concentration of 100,000 copies/ml. The frequency of each mutation detected in the original population at greater than or equal to 1% of the population, threshold calculated based on the intrinsic error rate of the assay, is indicated (mean±standard deviation, from quadruplicate experiments in the case of the experiment using mixtures of HIV-infected plasma). Amino acid substitutions detected at a frequency below 90% of the population are indicated.

FIGS. 4(A-E) illustrate schema and plots showing the reproducibility of the assay described herein. (A) Samples from two antiretroviral-naïve (NL4-3 and 12-596) and two antiretroviral-experienced (08-198 and 12-069) individuals were RT-PCR amplified in triplicate, each amplicon bar-coded four times, two DNA libraries prepared, and sequenced in duplicated for a total of 48 sequences per sample. (B) Neighbor-joining phylogenetic trees constructed using reads with a frequency >1 corresponding to 105 bp fragments from the protease, RT, integrase, and V3 regions. Each dot represents a unique variant, frequency is not depicted. Bootstrap resampling (1,000 data sets) of the multiple alignments tested the statistical robustness of the trees, with percentage values above 75% indicated by an asterisk. s/nt, substitutions per nucleotide. (C) Pearson correlation coefficient was used to determine the strength of association between the frequency of each nucleotide at each position among the 16 sequences obtained for each one of triplicate amplicons (n=48) for all four viruses in the gag-p2/NCp7/p1/p6/pol-PR/RT/IN and env-V3 regions. Over 135,000 and 5,000 points are included in each one of the gag-p2/NCp7/p1/p6/pol-PR/RT/IN and env-V3 plots, respectively. r, correlation coefficient; p, two-tailed p value. (D) Amino acids detected in codons associated with drug resistance in the protease, RT, and integrase regions according to the IAS-USA. Drug resistance mutations with a frequency ≥20%, <20% or any other amino acid changes are indicated. Only amino acid substitutions with a frequency >1% are depicted. (E) Frequency of amino acids in positions associated with drug resistance (gag-p2/NCp7/p1/p6/pol-PR/RT/IN) or X4 variants (env-V3) found in any of the four samples. Each dot represents the mean and 95% confidence intervals, with the exception of the insert (sample 12-069) where each dot indicates the frequency of amino acids detected in each of the 48 replicates, including their mean±standard deviation.

FIGS. 5(A-B) illustrate plots and graphs showing the comparison of the HIV-1 genotyping and coreceptor tropism assay with other HIV-1 genotypic phenotypic tests. Plasma samples from 166 treatment-experienced HIV-infected individuals from two cohorts of patients (Seville and Madrid) were analyzed as described in the Example. (A) Top two plots compare the number of drug resistance mutations detected by standard population (Sanger) and deep sequencing in each patient. The total numbers of drug resistance mutations identified by each sequencing method are indicated. The difference in the numbers of drug resistance mutations (mean±standard deviation) detected by population and deep sequencing in the protease (PR), reverse transcriptase (RT), and integrase (INT) regions is indicated in the bottom two plots. Mean values are indicated. Statistically significantly differences are marked with an asterisk (Paired t test, p<0.0001). Deep, deep sequencing; Pop, population sequencing (B) Hierarchical clustering analysis was used to group the different HIV-1 coreceptor tropism determinations by similarity. Dendograms were calculated using the Euclidean distance and Complete cluster methods with 100 bootstrap iterations as described (http://www.hiv.lanl.gov/content/sequence/HEATMAP/heatmap.html). Bootstrap values above 60% are indicated with an asterisk. Blocks indicate the absence or presence of non-R5 (X4) viruses, respectively, as determined by each assay. Concordance between DEEPGEEN HIV and the other HIV-1 coreceptor tropism assays are indicated. G2Pclin, Geno2Pheno with a FPR of 10%; MCT, 8-day maraviroc monotherapy clinical test; ESTA, enhanced sensitivity Trofile assay; Trofile, the original version of the Trofile assay; VeriTrop, phenotypic HIV-1 tropism assay; G2Pmot, Geno2Pheno with a FPR of 2.5% and 5.75% based on optimized cutoffs associated with the analysis of clinical data from MOTIVATE.

DETAILED DESCRIPTION

Figure 1:
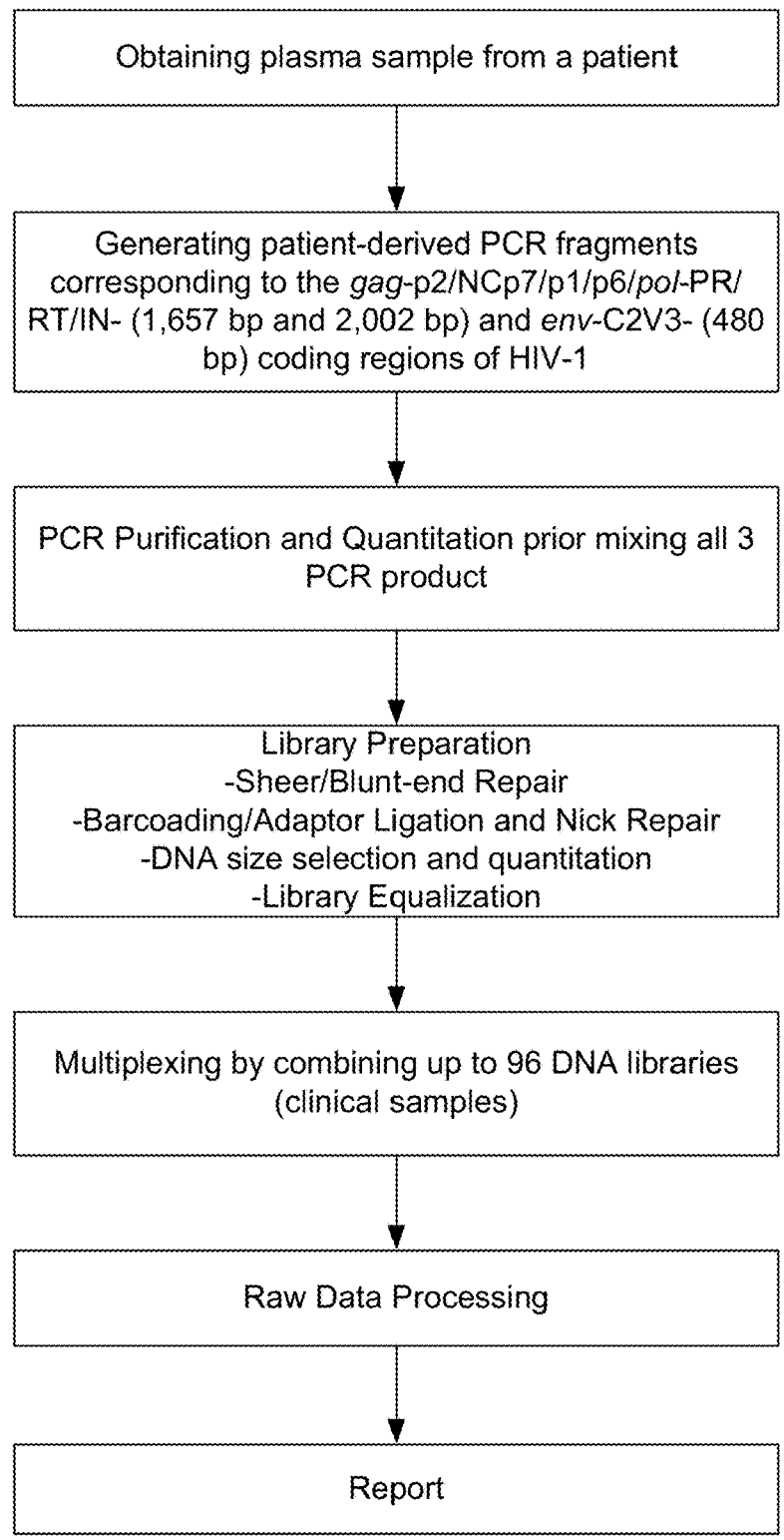
FIG. 1 illustrates a flow diagram showing an overview of the protocol for the HIV-1 genotyping and coreceptor tropism assay (DEEPGEEN HIV). Three PCR products corresponding to the gag-p2/NCp7/p1/p6/pol-PR/RT/IN-(1,657 bp and 2,002 bp) and env-C2V3-(480 bp) coding regions of HIV-1 were used to construct a multiplexed library for shotgun sequencing on the Ion PGM. Signal processing and base calling was performed with Torrent Analysis Suite version 3.4.2 and sequences analyzed using DEEPGEN Software Tool Suite. The HIVdb Program Genotypic Resistance Interpretation Algorithm from the Stanford University HIV Drug Resistance Database and Geno2Pheno were used to infer the levels of susceptibility to PI, RTI, and INI and for HIV-1 coreceptor tropism determination, respectively.

The following description of various embodiments is exemplary and explanatory only and is not to be construed as limiting or restrictive in any way. Other embodiments, features, objects, and advantages of the present teachings will be apparent from the description and accompanying drawings, and from the claims.

As used herein, "amplify", "amplifying" or "amplification reaction" and their derivatives, refer generally to any action or process whereby at least a portion of a nucleic acid molecule (referred to as a template nucleic acid molecule) is replicated or copied into at least one additional nucleic acid molecule. The additional nucleic acid molecule optionally includes sequence that is substantially identical or substantially complementary to at least some portion of the template nucleic acid molecule. The template nucleic acid molecule can be single-stranded or double-stranded and the additional nucleic acid molecule can independently be single-stranded or double-stranded. In some embodiments, amplification includes a template-dependent in vitro enzyme-catalyzed reaction for the production of at least one copy of at least some portion of the nucleic acid molecule or the production of at least one copy of a nucleic acid sequence that is complementary to at least some portion of the nucleic acid molecule. Amplification optionally includes linear or exponential replication of a nucleic acid molecule. In some embodiments, such amplification is performed using isothermal conditions; in other embodiments, such amplification can include thermocycling. In some embodiments, the amplification is a multiplex amplification that includes the simultaneous amplification of a plurality of target sequences in a single amplification reaction. At least some of the target sequences can be situated on the same nucleic acid molecule or on different target nucleic acid molecules included in the single amplification reaction. In some embodiments, "amplification" includes amplification of at least some portion of DNA- and RNA-based nucleic acids alone, or in combination. The amplification reaction can include single or double-stranded nucleic acid substrates and can further including any of the amplification processes known to one of ordinary skill in the art. In some embodiments, the amplification reaction includes polymerase chain reaction (PCR).

As used herein, "amplification conditions" and its derivatives, generally refers to conditions suitable for amplifying one or more nucleic acid sequences. Such amplification can be linear or exponential. In some embodiments, the amplification conditions can include isothermal conditions or alternatively can include thermocycling conditions, or a combination of isothermal and thermocycling conditions. In some embodiments, the conditions for amplifying one or more nucleic acid sequences include polymerase chain reaction (PCR) conditions. Typically, the amplification conditions refer to a reaction mixture that is sufficient to amplify nucleic acids such as one or more target sequences, or to amplify an amplified target sequence ligated to one or more adapters, e.g., an adapter-ligated amplified target sequence. Generally, the amplification conditions include a catalyst for amplification or for nucleic acid synthesis, for example a polymerase; a primer that possesses some degree of complementarity to the nucleic acid to be amplified; and nucleotides, such as deoxyribonucleotide triphosphates (dNTPs) to promote extension of the primer once hybridized to the nucleic acid. The amplification conditions can require hybridization or annealing of a primer to a nucleic acid, extension of the primer and a denaturing step in which the extended primer is separated from the nucleic acid sequence undergoing amplification. Typically, but not necessarily, amplification conditions can include thermocycling; in some embodiments, amplification conditions include a plurality of cycles where the steps of annealing, extending and separating are repeated. Typically, the amplification conditions include cations such as $Mg^{++}$ or $Mn^{++}$ (e.g., $MgCl_2$, etc) and can also include various modifiers of ionic strength.

As used herein, "target sequence" or "target sequence of interest" and its derivatives, refers generally to any single or double-stranded nucleic acid sequence that can be amplified or synthesized according to the disclosure, including any nucleic acid sequence suspected or expected to be present in a sample. In some embodiments, the target sequence is present in double-stranded form and includes at least a portion of the particular nucleotide sequence to be amplified or synthesized, or its complement, prior to the addition of target-specific primers or appended adapters. Target sequences can include the nucleic acids to which primers useful in the amplification or synthesis reaction can hybridize prior to extension by a polymerase. In some embodiments, the term refers to a nucleic acid sequence whose sequence identity, ordering or location of nucleotides is determined by one or more of the methods of the disclosure.

As defined herein, "sample" and its derivatives, is used in its broadest sense and includes any specimen, culture and the like that is suspected of including a target. In some embodiments, the sample comprises DNA, RNA, PNA, LNA, chimeric, hybrid, or multiplex-forms of nucleic acids. The sample can include any biological, clinical, surgical, agricultural, atmospheric or aquatic-based specimen containing one or more nucleic acids. The term also includes any isolated nucleic acid sample such a genomic DNA, fresh-frozen or formalin-fixed paraffin-embedded nucleic acid specimen.

As used herein, the term "primer" and its derivatives refer generally to any polynucleotide that can hybridize to a target sequence of interest. In some embodiments, the primer can also serve to prime nucleic acid synthesis. Typically, the primer functions as a substrate onto which nucleotides can be polymerized by a polymerase; in some embodiments, however, the primer can become incorporated into the synthesized nucleic acid strand and provide a site to which another primer can hybridize to prime synthesis of a new strand that is complementary to the synthesized nucleic acid molecule. The primer may be comprised of any combination of nucleotides or analogs thereof, which may be optionally linked to form a linear polymer of any suitable length. In some embodiments, the primer is a single-stranded oligonucleotide or polynucleotide. (For purposes of this disclosure, the terms "polynucleotide" and "oligonucleotide" are used interchangeably herein and do not necessarily indicate any difference in length between the two). In some embodiments, the primer is single-stranded but it can also be double-stranded. The primer optionally occurs naturally, as in a purified restriction digest, or can be produced synthetically. In some embodiments, the primer acts as a point of initiation for amplification or synthesis when exposed to amplification or synthesis conditions; such amplification or synthesis can occur in a template-dependent fashion and optionally results in formation of a primer extension product that is complementary to at least a portion of the target sequence. Exemplary amplification or synthesis conditions can include contacting the primer with a polynucleotide template (e.g., a template including a target sequence), nucleotides and an inducing agent such as a polymerase at a suitable temperature and pH to induce polymerization of nucleotides onto an end of the target-specific primer. If double-stranded, the primer can optionally be treated to separate its strands before being used to prepare primer extension products. In some embodiments, the primer is an oligodeoxyribonucleotide or an oligoribonucleotide. In some embodiments, the primer can include one or more nucleotide analogs. The exact length and/or composition, including sequence, of the target-specific primer can influence many properties, including melting temperature (Tm), GC content, formation of secondary structures, repeat nucleotide motifs, length of predicted primer extension products, extent of coverage across a nucleic acid molecule of interest, number of primers present in a single amplification or synthesis reaction, presence of nucleotide analogs or modified nucleotides within the primers, and the like. In some embodiments, a primer can be paired with a compatible primer within an amplification or synthesis reaction to form a primer pair consisting or a forward primer and a reverse primer. In some embodiments, the forward primer of the primer pair includes a sequence that is substantially complementary to at least a portion of a strand of a nucleic acid molecule, and the reverse primer of the primer of the primer pair includes a sequence that is substantially identical to at least of portion of the strand. In some embodiments, the forward primer and the reverse primer are capable of hybridizing to opposite strands of a nucleic acid duplex. Optionally, the forward primer primes synthesis of a first nucleic acid strand, and the reverse primer primes synthesis of a second nucleic acid strand, wherein the first and second strands are substantially complementary to each other, or can hybridize to form a double-stranded nucleic acid molecule. In some embodiments, one end of an amplification or synthesis product is defined by the forward primer and the other end of the amplification or synthesis product is defined by the reverse primer. In some embodiments, where the amplification or synthesis of lengthy primer extension products is required, such as amplifying an exon, coding region, or gene, several primer pairs can be created than span the desired length to enable sufficient amplification of the region. In some embodiments, a primer can include one or more cleavable groups. In some embodiments, primer lengths are in the range of about 10 to about 60 nucleotides, about 12 to about 50 nucleotides and about 15 to about 40 nucleotides in length. Typically, a primer is capable of hybridizing to a corresponding target sequence and undergoing primer extension when exposed to amplification conditions in the presence of dNTPS and a polymerase. In some instances, the particular nucleotide sequence or a portion of the primer is known at the outset of the amplification reaction or can be determined by one or more of the methods disclosed herein. In some embodiments, the primer includes one or more cleavable groups at one or more locations within the primer.

As used herein, "polymerase" and its derivatives, generally refers to any enzyme that can catalyze the polymerization of nucleotides (including analogs thereof) into a nucleic acid strand. Typically but not necessarily, such nucleotide polymerization can occur in a template-dependent fashion. Such polymerases can include without limitation naturally occurring polymerases and any subunits and truncations thereof, mutant polymerases, variant polymerases, recombinant, fusion or otherwise engineered polymerases, chemically modified polymerases, synthetic molecules or assemblies, and any analogs, derivatives or fragments thereof that retain the ability to catalyze such polymerization. Optionally, the polymerase can be a mutant polymerase comprising one or more mutations involving the replacement of one or more amino acids with other amino acids, the insertion or deletion of one or more amino acids from the polymerase, or the linkage of parts of two or more polymerases. Typically, the polymerase comprises one or more active sites at which nucleotide binding and/or catalysis of nucleotide polymerization can occur. Some exemplary polymerases include without limitation DNA polymerases and RNA polymerases. The term "polymerase" and its variants, as used herein, also refers to fusion proteins comprising at least two portions linked to each other, where the first portion comprises a peptide that can catalyze the polymerization of nucleotides into a nucleic acid strand and is linked to a second portion that comprises a second polypeptide. In some embodiments, the second polypeptide can include a reporter enzyme or a processivity-enhancing domain. Optionally, the polymerase can possess 5' exonuclease activity or terminal transferase activity. In some embodiments, the polymerase can be optionally reactivated, for example through the use of heat, chemicals or re-addition of new amounts of polymerase into a reaction mixture. In some embodiments, the polymerase can include a hot-start polymerase or an aptamer based polymerase that optionally can be reactivated.

The term "portion" or "region" and its variants, as used herein, when used in reference to a given nucleic acid molecule, for example a primer or a template nucleic acid molecule, comprises any number of contiguous nucleotides within the length of the nucleic acid molecule, including the partial or entire length of the nucleic acid molecule.

As used herein, the term "end" and its variants, when used in reference to a nucleic acid molecule, for example a target sequence or amplified target sequence, can include the terminal 30 nucleotides, the terminal 20 and even more typically the terminal 15 nucleotides of the nucleic acid molecule. A linear nucleic acid molecule comprised of linked series of contiguous nucleotides typically includes at least two ends. In some embodiments, one end of the nucleic acid molecule can include a 3' hydroxyl group or its equivalent, and can be referred to as the "3' end" and its derivatives. Optionally, the 3' end includes a 3' hydroxyl group that is not linked to a 5' phosphate group of a mononucleotide pentose ring. Typically, the 3' end includes one or more 5' linked nucleotides located adjacent to the nucleotide including the unlinked 3' hydroxyl group, typically the nucleotides located adjacent to the 3' hydroxyl, typically the terminal 20 and even more typically the terminal 15 nucleotides. In some embodiments, the term "3' end" for example when referring to a target-specific primer, can include the terminal 10 nucleotides, the terminal 5 nucleotides, the terminal 4, 3, 2 or fewer nucleotides at the 3' end. In some embodiments, the term "3' end" when referring to a target-specific primer can include nucleotides located at nucleotide positions 10 or fewer from the 3' terminus.

As used herein, "5' end", and its derivatives, generally refers to an end of a nucleic acid molecule, for example a target sequence or amplified target sequence, which includes a free 5' phosphate group or its equivalent. In some embodiments, the 5' end includes a 5' phosphate group that is not linked to a 3' hydroxyl of a neighboring mononucleotide pentose ring. Typically, the 5' end includes one or more linked nucleotides located adjacent to the 5' phosphate, typically the 30 nucleotides located adjacent to the nucleotide including the 5' phosphate group, typically the terminal 20 and even more typically the terminal 15 nucleotides. Generally, the one or more linked nucleotides can be represented as a percentage of the nucleotides present in the oligonucleotide or can be provided as a number of linked nucleotides adjacent to the 5' phosphate. For example, the 5' end can be less than 50% of the nucleotide length of an oligonucleotide. In another exemplary embodiment, the 5' end can include about 15 nucleotides adjacent to the nucleotide including the terminal 5' phosphate. In some embodiments, the 5' end does not include any unlinked 5' phosphate group but can include any moiety capable of serving as a site of attachment to a 3' hydroxyl group, or to the 3' end of another nucleic acid molecule. In some embodiments, the term "5' end" for example when referring to a target-specific primer, can include the terminal 10 nucleotides, the terminal 5 nucleotides, the terminal 4, 3, 2 or fewer nucleotides at the 5' end. In some embodiments, the term "5' end" when referring to a target-specific primer can include nucleotides located at positions 10 or fewer from the 5' terminus. In some embodiments, the 5' end of a target-specific primer can include only non-cleavable nucleotides, for example nucleotides that do not contain one or more cleavable groups as disclosed herein, or a cleavable nucleotide as would be readily determined by one of ordinary skill in the art.

As used herein, the term "nucleic acid" refers to natural nucleic acids, artificial nucleic acids, analogs thereof, or combinations thereof, including polynucleotides and oligonucleotides. As used herein, the terms "polynucleotide" and "oligonucleotide" are used interchangeably and mean single-stranded and double-stranded polymers of nucleotides including, but not limited to, 2'-deoxyribonucleotides (nucleic acid) and ribonucleotides (RNA) linked by internucleotide phosphodiester bond linkages, e.g., 3'-5' and 2'-5', inverted linkages, e.g., 3'-3' and 5'-5', branched structures, or analog nucleic acids. Polynucleotides have associated counter ions, such as $H^+$, $NH_4^+$, trialkylammonium, $Mg^{2+}$, $Na^+$ and the like. An oligonucleotide can be composed entirely of deoxyribonucleotides, entirely of ribonucleotides, or chimeric mixtures thereof. Oligonucleotides can be comprised of nucleobase and sugar analogs. Polynucleotides typically range in size from a few monomeric units, e.g., 5-40, when they are more commonly frequently referred to in the art as oligonucleotides, to several thousands of monomeric nucleotide units, when they are more commonly referred to in the art as polynucleotides; for purposes of this disclosure, however, both oligonucleotides and polynucleotides may be of any suitable length. Unless denoted otherwise, whenever a oligonucleotide sequence is represented, it will be understood that the nucleotides are in 5' to 3' order from left to right and that "A" denotes deoxyadenosine, "C" denotes deoxycytidine, "G" denotes deoxyguanosine, "T" denotes thymidine, and "U" denotes deoxyuridine. Oligonucleotides are said to have "5' ends" and "3' ends" because mononucleotides are typically reacted to form oligonucleotides via attachment of the 5' phosphate or equivalent group of one nucleotide to the 3' hydroxyl or equivalent group of its neighboring nucleotide, optionally via a phosphodiester or other suitable linkage.

As used herein, the term "polymerase chain reaction" ("PCR") refers to the method of K. B. Mullis U.S. Pat. Nos. 4,683,195 and 4,683,202, hereby incorporated by reference, which describe a method for increasing the concentration of a segment of a polynucleotide of interest in a mixture of genomic DNA without cloning or purification. This process for amplifying the polynucleotide of interest consists of introducing a large excess of two oligonucleotide primers to the DNA mixture containing the desired polynucleotide of interest, followed by a precise sequence of thermal cycling in the presence of a DNA polymerase. The two primers are complementary to their respective strands of the double stranded polynucleotide of interest. To effect amplification, the mixture is denatured and the primers then annealed to their complementary sequences within the polynucleotide of interest molecule. Following annealing, the primers are extended with a polymerase to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired polynucleotide of interest. The length of the amplified segment of the desired polynucleotide of interest (amplicon) is determined by the relative positions of the primers with respect to each other, and therefore, this length is a controllable parameter. By virtue of repeating the process, the method is referred to as the "polymerase chain reaction" (hereinafter "PCR"). Because the desired amplified segments of the polynucleotide of interest become the predominant nucleic acid sequences (in terms of concentration) in the mixture, they are said to be "PCR amplified". As defined herein, target nucleic acid molecules within a sample including a plurality of target nucleic acid molecules are amplified via PCR. In a modification to the method discussed above, the target nucleic acid molecules can be PCR amplified using a plurality of different primer pairs, in some cases, one or more primer pairs per target nucleic acid molecule of interest, thereby forming a multiplex PCR reaction. Using multiplex PCR, it is possible to simultaneously amplify multiple nucleic acid molecules of interest from a sample to form amplified target sequences. It is also possible to detect the amplified target sequences by several different methodologies (e.g., quantitation with a bioanalyzer or qPCR, hybridization with a labeled probe; incorporation of biotinylated primers followed by avidin-enzyme conjugate detection; incorporation of $^{32}$P-labeled deoxynucleotide triphosphates, such as dCTP or dATP, into the amplified target sequence). Any oligonucleotide sequence can be amplified with the appropriate set of primers, thereby allowing for the amplification of target nucleic acid molecules from genomic DNA, cDNA, formalin-fixed paraffin-embedded DNA, fine-needle biopsies and various other sources. In particular, the amplified target sequences created by the multiplex PCR process as disclosed herein, are themselves efficient substrates for subsequent PCR amplification or various downstream assays or manipulations.

As defined herein "multiplex amplification" refers to selective and non-random amplification of two or more target sequences within a sample using at least one target-specific primer. In some embodiments, multiplex amplification is performed such that some or all of the target sequences are amplified within a single reaction vessel. The "plexy" or "plex" of a given multiplex amplification refers generally to the number of different target-specific sequences that are amplified during that single multiplex amplification. In some embodiments, the plexy can be about 12-plex, 24-plex, 48-plex, 96-plex, 192-plex, 384-plex, 768-plex, 1536-plex, 3072-plex, 6144-plex or higher.

Embodiments described herein relate assays, to systems, methods, and kits for targeted sequencing using nucleic acid primer specific to amplify sequence regions comprising HIV variants, and using those amplified sequence regions for highly sensitive detection of the HIV variants in viral samples obtained from a subject. In particular, embodiments described herein relate to methods of diagnosing a number of low frequency sequence variants in HIV drug resistance (e.g., allelic variants, single nucleotide polymorphism variants, indel variants) and non-R5 HIV variants by the identification of specific DNA, detecting each variant that is present in at least 1% of the population, and associating the detected variants with a therapeutic regimen. In one embodiment, one or more target regions from a representative proportion of the total population HIV virus in a sample are clonally replicated by polymerase chain reaction (PCR), where the clonal populations (also referred to as "amplicons") are each derived from a single viral particle. The clonal populations are sequenced in parallel to identify variants of previously known and unknown composition as well as the frequency of occurrence of each variant, which is representative of the frequency of the variants in the original sample. In some embodiments, the method can be used for detecting low frequency occurrence of one or more HIV sequence variants associated with drug resistance and HIV tropism, such as non-R5 HIV-1 variants.

As described herein, the methods employ nucleic acid primers specifically designed to amplify the Gag proteins p2, p7, p1 and p6, and the protease, reverse transcriptase, and integrase enzymes regions as well as the C2V3 region of HIV RNA or its complementary DNA. Also, the target sequences for the primers have been specifically selected because of their proximity to the target region, and because they exhibit a low rate of mutation that predictably enable primer hybridization and amplification of the target nucleic regions in an HIV nucleic acid population. Thousands of individual HIV amplicons are sequenced in a massively parallel, efficient, and cost effective manner to generate a distribution of the sequence variants found in the population of HIV viral particles. This methodology accurately provides drug resistance information for all protease, reverse transcriptase, integrase, and maturation inhibitors, as well as HIV-1 coreceptor tropism, in a single, more efficient, rapid, and affordable clinical assay In particular embodiments, the method described herein can include a two stage PCR technique (i.e., producing first and second amplicons) targeted to regions of HIV known to be associated with one or more HIV sequence variants associated with drug resistance and HIV tropism, coupled with a sequencing technique that produces sequence information from thousands of viral particles in parallel which enables identification of the one or more HIV sequence variants associated with drug resistance and HIV tropism, even those types occurring at a low frequency in a sample. In fact, embodiments described herein can detect one or more HIV sequence variants associated with drug resistance and HIV tropism which are present in a sample containing HIV viral particles in non-stoichiometric allele amounts, such as, for example, HIV tropism variants present in less than 50%, less than 25%, less than 10%, less than 5% or less than 1% of the viral population. The PCR technique employed herein is not only reproducible but ensures successful amplification of samples from diverse HIV-1 subtypes while avoiding amplification of non-specific products from endogenous or any of the related viruses tested.

In some embodiments, the method can include generating a plurality of cDNA species from a plurality of RNA molecules in an HIV sample population. For example, the source of HIV sample may be a tissue or body fluid (e.g., blood or plasma sample) from a patient/subject, or other organism susceptible to HIV infection.

Also in some embodiments, RNA molecules may be collected from multiple organisms. For example, allelic frequency of a population of 1000 individuals may be performed in one experiment analyzing a mixed sample from 1000 individuals. Naturally, for a mixed sample to be representative of the allelic frequency of a population, each member of the population (each individual) must contribute the same (or approximately the same) amount of nucleic acid (same number of copies of an allele) to the pooled sample.

In another embodiment, the RNA molecules in a single individual may be determined. That is, the RNA molecules may be isolated from a single individual.

In some embodiments, the RNA molecules may include viral RNA, such as an HIV viral isolate. In some embodiments, the "target population", "sample population", or "subject population" may be derived from an HIV RNA source comprising a detectable titer of virus. In typical embodiments, the source may include a sample from a human subject that includes collected tissue or fluid samples from an HIV infected patient that may or may not have been exposed to a drug treatment regimen (i.e., the patient may or may not be "drug naive"). Also, the methods described herein can determine if variation is present at a low frequency in the sample, where the variations may be correlated with known drug resistance or newly identified resistant strains. The methods also provide a measure of frequency of each of the variants in a sample population that can be employed to determine or alter a therapeutic regimen that may include avoidance of one or more drugs, drug classes, or drug combinations that will have little therapeutic benefit due to resistance conferred by the identified HIV variant strain(s).

The plurality of cDNA species can be generated from the plurality of RNA molecules by any art-recognized method. Alternatively, template libraries can be made by generating a complementary DNA (cDNA) library from RNA, e.g., messenger RNA (mRNA). Methods of sample preparation may be found in U.S. Pat. No. 7,323,305 and co-pending PCT application US04/02570 and is also published in WO/04070007, all incorporated herein by reference in their entirety.

A plurality of first amplicons and second amplicons can then be amplified from the cDNA species. The first amplicons can be amplified using first pairs of primers that amplify a HIV genomic region of the cDNA species encoding the Gag proteins p2, p7, p1 and p6, and the protease, reverse transcriptase, and integrase enzymes. The second amplicons can be amplified using second pairs of primers that amplify a HIV genomic encoding region of the cDNA species encoding env-C2V3 region.

In some embodiments, the first amplicons can include a first and second overlapping amplicon fragments corresponding to the genomic region encoding p2 to 5' region of reverse transcriptase enzyme and the genomic region encoding 3' region of reverse transcriptase enzyme to integrase enzyme. Alternatively, it may be advantageous to produce different amplicon products using different primer combinations, such as amplicon products having a short amplicon product within the region covered by a long amplicon product where the region covered by the short product is represented in both amplicons. Both strategies provide regions with "double coverage" by the amplicons, which is beneficial in the event that one of the amplicon products fails to amplify properly.

Those of ordinary skill in the related art will also appreciate that a "nested" type amplification strategy may be employed using primers described herein. For example, nested PCR strategies are generally employed to reduce the effects of contamination typically caused by multiple primer binding sites and the generation of undesirable amplification products. In the present example, a first set of amplification products may be produced using a forward primer and reverse primer, which may contain some of the undesirable product. A second round of amplification using forward primers and reverse primers and the first set of amplification products may then be executed where it is unlikely that the undesirable products of the first set would have binding sites for primers of the second set resulting in a set of amplification products with much higher specificity to the desired target region.

By way of example, the HIV-1 genomic region encoding the Gag proteins p2, p7, p1 and p6, and the protease, reverse transcriptase, and integrase enzymes was amplified as two overlapping fragments (1,657 nt and 2,002 nt corresponding to the p2-5'half RT and 3'half RT-INT, respectively) using a series of external and nested primers with defined cycling conditions. External PCR reactions were carried out in a 50-µl mixture containing 0.2 mM dNTPs, 1 mM MgCl2 and 2.5 units of Pfu Turbo DNA Polymerase (Stratagene). Nested PCR reactions were carried out in 50-µl mixture containing 0.2 mM dNTPs, 0.3 units of Pfu Turbo DNA Polymerase and 1.9 units of Taq Polymerase (Denville Scientific; Metuchen, N.J.). A fragment corresponding to the C2V3 region (480 nt) of the surface glycoprotein (gp120) in the envelope gene can be amplified using a series of external and nested primers with defined cycling.

The nucleic acid sequence compositions of the first amplicons and second amplicons can then be determined using next generation sequencing methods, such as massively parallel signature sequencing (MPSS), polony sequencing, pyrosequencing, Illumina dye sequencing, SOLiD sequencing, nanopore sequencing, semiconductor sequencing (Ion Torrent), sequencing-by-ligation, sequencing-by-hybridization, RNA-Seq (Illumina), Digital Gene Expression (Helicos), and Single Molecule Sequencing by Synthesis (SMSS) (Helicos), Clonal Single Molecule Array (Solexa), shotgun sequencing, and Maxim-Gilbert sequencing.

For example, a mixture of all three purified DNA amplicons can be randomly fragmented and blunt-ends repaired using the Ion Shear Plus Reagent (Life Technologies) followed by DNA purification (Agencourt AMPure XP, Beckman Coulter). The P1 adapter (5'-CCA CTA CGC CTC CGC TTT CCT CTC TAT GGG CAG TCG GTG AT (SEQ ID NO: 1); 5'-ATC ACC GAC TGC CCA TAG AGA GGA AAG CGG AGG CGT AGT GG*T*T (SEQ ID NO: 2)) and one of 96 barcodes can be ligated to the repaired fragment ends prior to DNA purification (Agencourt AMPure XP, Beckman Coulter). DNA fragments can then be selected by size (i.e., 300 bp; Pippin Prep™, Life Technologies) and each barcoded library, i.e., a mixture of all three amplicons per sample, can be purified (Agencourt AMPure XP, Beckman Coulter) and normalized using the Ion Library Equalizer™ Kit (Life Technologies). All barcoded DNA libraries, corresponding to patient-derived amplicons plus the HIV-1NL4-3 control, can then be pooled in equimolar concentrations and templates prepared and enriched for sequencing on Ion Sphere Particles (ISPs) using the Ion OneTouch 200 Template Kit v2 (Life Technologies) in the Ion OneTouch 2 System (Life Technologies). Templated ISPs can be quantified (Qubit 2.0, Life Technologies) and loaded into an Ion 318™ Chip (Life Technologies) to be sequenced on the Ion PGM™ using the Ion PGM™ Sequencing 200 Kit v2 (Life Technologies). A signal processing and base calling can then be performed with Torrent Analysis Suite version 3.4.2 to determine the nucleic acid sequences of the amplicons.

A guide sequence with minimal divergence from the determined nucleic acid sequence composition can be selected for mapping variants of the determined nucleic acid compositions by comparing the determined nucleic acid sequence compositions to reference sequences. Selection of a guide sequence for mapping can minimize the amount of data loss during mapping due to the high HIV-1 sequence variability and allow for inter-patient indel variation across the gag-p2/NCp7/p1/p6/pol-PR/RT/IN and env-C2V3-coding regions. In some embodiments, sample-specific reference sequences can be constructed for each one of these two genomic regions, i.e., positions 1,807 to 5,096 and 6,900 to 7,400, in the HXB2 reference strain (GenBank accession no. K03455), respectively.

A guide template for mapping can selected from a reference database, such as the Los Alamos HIV Sequence Database (http://www.hiv.lanl.gov/content/sequence/HIV/mainpage.html) by, for example, comparing 100 randomly selected reads to the corresponding region within all full-length sequences present within the HIV Sequence Database. This comparison can be performed by rapidly identifying regions of similarity between any two sequences to select a guide sequence for mapping with minimal divergence from the read data. Following the selection of a guide sequence, reads can be mapped and aligned using a mapping algorithm. Reads spanning the 3'end of Gag, PR, RT, and INT were then translated and assembled for genotyping.

Variants at least 1% in the determined nucleic acid sequence compositions are identified by comparing the determined nucleic sequence to the guide sequence. The identification and calculation of the frequency of each amino acid present in each genomic position, can be calculated using as input a table, which includes the nucleotide frequencies at each position relative to the reference sequence. Coverage, indel, codon, and residue frequencies at each position can also be listed. In some embodiments, the results can be summarized in a graphical interface with particular focus on sites of known drug resistance based on the latest edition of the IAS-USA HIV Drug Resistance Mutations list. A list of the amino acids at these positions, and their frequencies, can be exported as a tabulated text file and used with the HIVdb Program Genotypic Resistance Interpretation Algorithm from the Stanford University HIV Drug Resistance Database (http://hivdb.stanford.edu) to infer the levels of susceptibility to protease, reverse transcriptase, and integrase inhibitors.

HIV-1 co-receptor tropism can also predicted from population and deep sequencing V3 sequences using tropism prediction algorithms PSSM http://ubik.microbiol.washington.edu/computing/pssm/ and Geno2Pheno (G2P), which are publicly available. In some embodiments, plasma samples were classified as containing non-R5 viruses if at least 2% of the individual sequences, as determined by deep sequencing, were predicted to be non-R5

Typically, one or more instrument elements may be employed that automate one or more process steps. For example, embodiments of a sequencing method may be executed using instrumentation to automate and carry out some or all process steps. Embodiments of sequencing instrument employed to execute sequencing processes may include various fluidic components in the fluidic subsystem, various optical components in the optic subsystem, as well as additional components that may include microprocessor and/or microcontroller components for local control of some functions. Further, the sequencing instrument may be operatively linked to one or more external computer components, such as a computer that may for instance execute system software or firmware such as application that may provide instructional control of one or more of the components and/or some data analysis functions.

In some embodiments, following determination of variants in the assayed HIV-1 from a sample obtained from the subject, a therapeutic regimen can be administered to treat the subject with HIV-1 based on the detected variant. For example, where the variant corresponds to a CCR5 tropic virus, a CCR5 antagonist can be administered to the subject.

In other examples, where detected variants correspond to drug resistance to, for example, protease (PI), nucleoside/nucleotide reverse transcriptase (NRTI), nonnucleoside reverse transcriptase (NNRTI), integrase (INI), fusion (FI), and entry (EI), inhibitors, a therapeutic regimen can be administered to treat the subject with HIV-1 based on the detected resistance.

It will be appreciated that one or more known HIV-1/AIDS drugs or antiviral agents may be administered to the subject with HIV-1/AIDS based on the detected variants or resistance. It will be understood that the HIV/AIDS antivirals can be coadministered in combination with any immunomodulators, anti-infectives or vaccines. The HIV/AIDS antivirals employed in these combinations is not limited to the following list, and includes in principle any pharmaceutical composition useful for the treatment of AIDS. The HIV/AIDS antivirals and other agents will typically be employed in these combinations in their conventional dosage ranges and regimens as reported in the art.

Examples of antiviral agents include (but not restricted) ANTIVIRALS Manufacturer (Tradename and/or Drug Name Location) Indication (Activity): abacavir GlaxoSmithKline HIV infection, AIDS, ARC GW 1592 (ZIAGEN) (nRTI); 1592U89 abacavir+GlaxoSmithKline HIV infection, AIDS, ARC (nnRTI); lamivudine+(TRIZIVIR) zidovudine acemannan Carrington Labs ARC (Irving, Tex.) ACH 126443 Achillion Pharm. HIV infections, AIDS, ARC (nucleoside reverse transcriptase inhibitor); acyclovir Burroughs Wellcome HIV infection, AIDS, ARC, in combination with AZT AD-439 Tanox Biosystems HIV infection, AIDS, ARC AD-519 Tanox Biosystems HIV infection, AIDS, ARC adefovir dipivoxil Gilead HIV infection, AIDS, ARC GS 840 (RTI); AL-721 Ethigen ARC, PGL, HIV positive, (Los Angeles, Calif.), AIDS alpha interferon GlaxoSmithKline Kaposi's sarcoma, HIV, in combination w/Retrovir AMD3100 AnorMed HIV infection, AIDS, ARC (CXCR4 antagonist); amprenavir GlaxoSmithKline HIV infection, AIDS, 141 W94 (AGENERASE) ARC (PI); GW 141 VX478 (Vertex) ansamycin Adria Laboratories ARC LM 427 (Dublin, Ohio) Erbamont (Stamford, Conn.) antibody which neutralizes; Advanced Biotherapy AIDS, ARC pH labile alpha aberrant Concepts (Rockville, Interferon Md.) AR177 Aronex Pharm HIV infection, AIDS, ARC atazanavir (BMS 232632) Bristol-Myers-Squibb HIV infection, AIDS, ARC (ZRIVADA) (PI); beta-fluoro-ddA Nat'l Cancer Institute AIDS-associated diseases BMS-232623 Bristol-Myers Squibb/HIV infection, AIDS, (CGP-73547) Novartis ARC (PI); BMS-234475 Bristol-Myers Squibb/HIV infection, AIDS, (CGP-61755) Novartis ARC (PI); capravirine Pfizer HIV infection, AIDS, (AG-1549, S-1153) ARC (nnRTI); CI-1012 Warner-Lambert HIV-1 infection cidofovir Gilead Science CMV retinitis, herpes, papillomavirus curdlan sulfate AJI Pharma USA HIV infection cytomegalovirus immune MedImmune CMV retinitis globin cytovene Syntex sight threatening CMV ganciclovir peripheral CMV retinitis delavirdine Pharmacia-Upjohn HIV infection, AIDS, (RESCRIPTOR) ARC (nnRTI); dextran Sulfate Ueno Fine Chem. Ind. AIDS, ARC, HIV Ltd. (Osaka, Japan) positive asymptomatic ddC Hoffman-La Roche HIV infection, AIDS, ARC (zalcitabine, (HIVID) (nRTI); dideoxycytidine ddI Bristol-Myers Squibb HIV infection, AIDS, ARC; Dideoxyinosine (VIDEX) combination with AZT/d4T (nRTI) DPC 681 & DPC 684 DuPont HIV infection, AIDS, ARC (PI) DPC 961 & DPC 083 DuPont HIV infection AIDS, ARC (nnRTRI); emvirine Triangle Pharmaceuticals HIV infection, AIDS, ARC (COACTINON) (non-nucleoside reverse transcriptase inhibitor); EL10 Elan Corp, PLC HIV infection (Gainesville, Ga.) efavirenz DuPont HIV infection, AIDS, (DMP 266) (SUSTIVA) ARC (nnRTI); Merck (STOCRIN) famciclovir Smith Kline herpes zoster, herpes simplex emtricitabine Triangle Pharmaceuticals HIV infection, AIDS, ARC FTC (COVIRACIL) (nRTI); Emory University emvirine Triangle Pharmaceuticals HIV infection, AIDS, ARC (COACTINON) (non-nucleoside reverse transcriptase inhibitor); HBY097 Hoechst Marion Roussel HIV infection, AIDS, ARC (nnRTI); hypericin VIMRx Pharm. HIV infection, AIDS, ARC recombinant human; Triton Biosciences AIDS, Kaposi's sarcoma, interferon beta (Almeda, Calif.); ARC interferon alfa-n3 Interferon Sciences ARC, AIDS indinavir; Merck (CRIXIVAN) HIV infection, AIDS, ARC, asymptomatic HIV positive, also in combination with AZT/ddI/ddC (PI); ISIS 2922 ISIS Pharmaceuticals CMV retinitis JE2147/AG1776; Agouron HIV infection, AIDS, ARC (PI); KNI-272 Nat'l Cancer Institute HIV-assoc. diseases lamivudine; 3TC Glaxo Wellcome HIV infection, AIDS, (EPIVIR) ARC; also with AZT (nRTI); lobucavir Bristol-Myers Squibb CMV infection; lopinavir (ABT-378) Abbott HIV infection, AIDS, ARC (PI); lopinavir+ritonavir Abbott (KALETRA) HIV infection, AIDS, ARC (ABT-378/r) (PI); mozenavir AVID (Camden, N.J.) HIV infection, AIDS, ARC (DMP-450) (PI); nelfinavir Agouron HIV infection, AIDS, (VIRACEPT) ARC (PI); nevirapine Boeheringer HIV infection, AIDS, Ingleheim ARC (nnRTI); (VIRAMUNE) novapren Novaferon Labs, Inc. HIV inhibitor (Akron, Ohio); pentafusaide Trimeris HIV infection, AIDS, ARC T-20 (fusion inhibitor); peptide T Peninsula Labs AIDS octapeptide (Belmont, Calif.) sequence PRO 542 Progenics HIV infection, AIDS, ARC (attachment inhibitor); PRO 140 Progenics HIV infection, AIDS, ARC (CCR5 co-receptor inhibitor); trisodium Astra Pharm. Products, CMV retinitis, HIV infection, phosphonoformate Inc other CMV infections; PNU-140690 Pharmacia Upjohn HIV infection, AIDS, ARC (PI); probucol Vyrex HIV infection, AIDS; RBC-CD4Sheffield Med. Tech HIV infection, AIDS, (Houston Tex.) ARC; ritonavir Abbott HIV infection, AIDS, (ABT-538) (RITONAVIR) ARC (PI); saquinavir Hoffmann-LaRoche HIV infection, AIDS, (FORTOVASE) ARC (PI); stavudine d4T Bristol-Myers Squibb HIV infection, AIDS, ARC didehydrodeoxy-(ZERIT.) (nRTI); thymidine T-1249 Trimeris HIV infection, AIDS, ARC (fusion inhibitor); TAK-779 Takeda HIV infection, AIDS, ARC (injectable CCR5 receptor antagonist); tenofovir Gilead (VIREAD) HIV infection, AIDS, ARC (nRTI); tipranavir (PNU-140690) Boehringer Ingelheim HIV infection, AIDS, ARC (PI); TMC-120 & TMC-125 Tibotec HIV infections, AIDS, ARC (nnRTI); TMC-126 Tibotec HIV infection, AIDS, ARC (PI); valaciclovir GlaxoSmithKline genital HSV & CMV infections virazole Viratek/ICN (Costa asymptomatic HIV positive, ribavirin Mesa, Calif.) LAS, ARC; zidovudine; AZT GlaxoSmithKline HIV infection, AIDS, ARC, (RETROVIR) Kaposi's sarcoma in combination with other therapies (nRTI); [PI=protease inhibitor nnRTI=non-nucleoside reverse transcriptase inhibitor NRTI=nucleoside reverse transcriptase inhibitor].

The HIV-1/AIDS antiviral agents may be used individually, sequentially, or in combination with one or more other such therapeutic agents described herein. Administration to a subject may be by the same or different route of administration or together in the same pharmaceutical formulation.

The dosage of HIV-1/AIDS antiviral agents administered can be dependent on the HIV-1 variants detected by the method described herein as well as on the body weight, age, individual condition, surface area of the area to be treated and on the form of administration. The size of the dose also will be determined by the existence, nature, and extent of any adverse effects that accompany the administration of a particular small molecule compound in a particular subject. Typically, a dosage of the active compounds described herein is a dosage that is sufficient to achieve the desired effect. Optimal dosing schedules can be calculated from measurements of compound accumulation in the body of a subject. In general, dosage may be given once or more daily, weekly, or monthly. Persons of ordinary skill in the art can easily determine optimum dosages, dosing methodologies and repetition rates.

EXAMPLE

In this Example, we developed, characterized, and validated a HIV-1 genotyping assay based on deep sequencing to simplify the monitoring of patients infected with HIV-1. This all-inclusive, sensitive methodology accurately provides drug resistance information for all protease, reverse transcriptase, integrase, and maturation inhibitors, as well as HIV-1 coreceptor tropism, in a single, more efficient, rapid, and affordable clinical assay.

Materials and Methods
Viruses and Plasmids

The following viruses were obtained from the AIDS Research and Reference Reagent Program, Division of AIDS, NIAID, NIH: HIV-$1_{A\text{-}92RW009}$, HIV-$1_{A\text{-}93RW020}$, HIV-$1_{A\text{-}92UG029}$, HIV-$1_{B\text{-}92BR014}$, HIV-$1_{B\text{-}92TH593}$, HIV-$1_{B\text{-}US714}$, HIV-$1_{B\text{-}92US727}$, HIV-$1_{B\text{-}92US076}$, HIV-$1_{C\text{-}92BR025}$, HIV-$1_{D\text{-}94UG108}$, HIV-$1_{D\text{-}92UG038}$, HIV-$1_{D\text{-}93UG065}$, HIV-$1_{F\text{-}93BR029}$, HIV-$1_{F\text{-}93BR020}$, HIV-$1_{G\text{-}RU570}$, HIV-$1_{G\text{-}RU132}$, HIV-$1_{AE\text{-}CMU02}$, HIV-$1_{AE\text{-}CMU06}$, HIV-$1_{AE\text{-}92TH021}$, HIV-$1_{BF\text{-}93BR029}$, and HIV-$2_{CBL\text{-}20}$ or Dr. Eric J. Arts' laboratory at Case Western Reserve University (CWRU), Cleveland, Ohio: HIV-$1_{A\text{-}V115}$, HIV-$1_{A\text{-}V120}$, HIV-$1_{C\text{-}C18}$, HIV-$1_{C\text{-}C20}$, HIV-$1_{C\text{-}C21}$, HIV-$1_{C\text{-}C22}$, HIV-$1_{D\text{-}V89}$, HIV-$1_{D\text{-}V122}$, HIV-$1_{D\text{-}V126}$, HIV-$1_{F\text{-}V1820}$, HIV-$1_{F\text{-}V164}$, HIV-$1_{F\text{-}CA16}$, and HIV-$1_{F\text{-}CA20}$. Aliquots of additional RNA or DNA viruses were obtained from the Molecular Diagnostics or Medical Microbiology laboratories at University Hospitals Case Medical Center (UHCMC), Cleveland, Ohio (BK virus, BKV; Cytomegalovirus, CMV; Herpes simplex virus 1 and 2, HSV-1 and HSV-2; and Varicella zoster virus, VZV) or the Division of Infectious Diseases, School of Medicine at CWRU (Hepatitis B virus, HBV; Hepatitis C virus, HCV; and Epstein-Barr virus, EBV). Plasmids containing patient-derived HIV-1 gag-p2/NCp7/p1/p6/pol-PR/RT/IN-coding sequences from multidrug-resistant viruses, i.e., 08-180 and 08-194 have been previously described, as well as a pNL4-3 plasmid containing the env gene from the R5 HIV-1YU2 virus. Five plasmid mixtures containing drug resistance mutations in the HIV-1 pol gene, i.e., K65R (5%)+wild type (95%), K103N (5%)+wild type (95%), K101E (5%)+E138K (5%)+wild type (90%), K101E+E138K (10%)+wild type (90%), and M184V (RT)+E92Q (IN) (10%)+wild type (90%) were obtained from Gilead Sciences, Inc. (Foster City, Calif.).

Clinical Samples

Plasma samples for the characterization and verification of the novel HIV-1 genotypic and coreceptor tropism assay were obtained during routine patient monitoring from a well-characterized cohort of HIV-infected individuals at the AIDS Clinical Trials Unit (ACTU) at CWRU/UHCMC, with the understanding and written consent of each participant. RNA specimens, derived from plasma samples collected from HIV-infected individuals enrolled in the (i) maraviroc expanded access program in Europe or (ii) ALLE- GRO trial, were obtained from the Hospital Carlos III (Madrid, Spain). Written informed consent was obtained from the patients before participation in the study as previously described. HIV-1 coreceptor tropism was determined at baseline using two phenotypic assays, i.e., the original version of the Trofile and VERITROP and by population sequencing analyzed with Geno2Pheno, with a false positive rate (FPR, predicted frequency of classifying an R5 sequence as non-R5 virus) based on optimized cutoffs associated with the analysis of clinical data from MOTIVATE (2.5% and 5.75%). Finally, plasma samples were obtained from HIV-infected individuals at the Infectious Diseases Unit Virgen del Rocio University Hospital (Sevilla, Spain) participating in a study to evaluate the use of an 8-day maraviroc monotherapy clinical test (MCT). Patients provided written informed consent and the ethical committee of the hospital approved the study. HIV-1 coreceptor tropism in these samples was determined at baseline using two different phenotypic assays, i.e., the enhanced sensitivity Trofile assay (ESTA) and Trocai and by population sequencing analyzed with Geno2Pheno, with a FPR of 10% following the recommendations from the European Consensus Group on clinical management of HIV-1 tropism testing as described in the Geno2Pheno website (http://coreceptor.bioinf.mpiinf.mpg.de/index.php).

Reverse Transcription (RT)-PCR Amplification of gag-p2/NCp7/p1/p6/pol-PR/RT/IN- and env-C2V3-Coding Regions Plasma viral RNA was purified from pelleted virus particles by centrifuging one milliliter of plasma at 18,000 g×60 min at 4° C., removing 860 µl of cell-free supernatant and resuspending the pellet in the remaining 140 µl, to finally extract viral RNA using QIAamp Viral RNA Mini kit (Qiagen; Valencia, Calif.). Viral RNA was reverse-transcribed using AccuScript High Fidelity Reverse Transcriptase (Stratagene Agilent; Santa Clara, Calif.) and the corresponding antisense external primers in 20 µl reaction mixture containing 1 mM dNTPs, 10 mM DTT and 10 units of RNase inhibitor. The HIV-1 genomic region encoding the Gag proteins p2, p7, p1 and p6, and the protease, reverse transcriptase, and integrase enzymes was amplified as two overlapping fragments (1,657 nt and 2,002 nt corresponding to the p2-5'half RT and 3'half RT-INT, respectively) using a series of external and nested primers with defined cycling conditions. External PCR reactions were carried out in a 50-µl mixture containing 0.2 mM dNTPs, 1 mM MgCl2 and 2.5 units of Pfu Turbo DNA Polymerase (Stratagene). Nested PCR reactions were carried out in 50-µl mixture containing 0.2 mM dNTPs, 0.3 units of Pfu Turbo DNA Polymerase and 1.9 units of Taq Polymerase (Denville Scientific; Metuchen, N.J.). A fragment corresponding to the C2V3 region (480 nt) of the surface glycoprotein (gp120) in the envelope gene was amplified using a series of external and nested primers with defined cycling conditions as previously described.

Population (Sanger) Sequencing Analysis

PCR products corresponding to the gag-p2/NCp7/p1/p6/pol-PR/RT/IN- and env-C2V3-coding regions of HIV-1 were purified with the QIAquick PCR Purification kit (Qiagen) and sequenced (Sanger, population, or global sequence) using AP Biotech DYEnamic ET Terminator cycle with Thermosequenase II (Davis Sequencing LCC, Davis, Calif.). Nucleotide sequences were analyzed using DNASTAR Lasergene Software Suite v.10.0.1 (Madison, Wis.).

Deep Sequencing of gag-p2/NCp7/p1/p6/pol-PR/RT/IN- and env-C2V3-Coding Regions

The three PCR products corresponding to the gag-p2/NCp7/p1/p6/pol-PR/RT/IN-(1,657 nt and 2,002 nt fragments) and env-C2V3-(480 nt fragment) coding regions of HIV-1 were purified (Agencourt AMPure XP, Beckman Coulter) and quantified (2100 Bioanalyzer DNA 7500, Agilent Technologies) prior to using the Ion Xpress Fragment Library Kit (Life Technologies, Carlsbad Calif.) to construct a multiplexed library for shotgun sequencing on the Ion Personal Genome Machine (PGM, Life Technologies) (FIG. 1). Briefly, a mixture of all three purified DNA amplicons (33 ng each) was randomly fragmented and blunt-ends repaired using the Ion Shear Plus Reagent (Life Technologies) followed by DNA purification (Agencourt AMPure XP, Beckman Coulter). The P1 adapter (5'-CCA CTA CGC CTC CGC TTT CCT CTC TAT GGG CAG TCG GTG AT (SEQ ID NO: 1); 5'-ATC ACC GAC TGC CCA TAG AGA GGA AAG CGG AGG CGT AGT GG*T*T) (SEQ ID NO: 2) and one of 96 barcodes were ligated to the repaired fragment ends prior to DNA purification (Agencourt AMPure XP, Beckman Coulter). DNA fragments were then selected by size (i.e., 300 bp; Pippin Prep, Life Technologies) and each barcoded library, i.e., a mixture of all three amplicons per sample, was purified (Agencourt AMPure XP, Beckman Coulter) and normalized using the Ion Library Equalizer Kit (Life Technologies). All barcoded DNA libraries, corresponding to patient-derived amplicons plus the HIV-1NL4-3 control, were pooled in equimolar concentrations and templates prepared and enriched for sequencing on the Ion Sphere Particles (ISPs) using the Ion OneTouch 200 Template Kit v2 (Life Technologies) in the Ion OneTouch 2 System (Life Technologies). Templated ISPs were quantified (Qubit 2.0, Life Technologies) and loaded into an Ion 318™ Chip (Life Technologies) to be sequenced on the Ion PGM using the Ion PGM Sequencing 200 Kit v2 (Life Technologies). Following a 4 hours and 20 minutes sequencing run, signal processing and base calling was performed with Torrent Analysis Suite version 3.4.2.

Read Mapping, Variant Calling, and Phylogenetic Analysis

As part of the novel HIV-1 genotypic and coreceptor tropism assay we developed the DEEPGEN Software Tool Suite for the processing of HIV-1 deep sequencing data and HIV-1 drug resistance determination. DEEPGEN uses two main tools: Viral Read Mapper and Variant Caller.

Viral Read Mapper

To minimize the amount of data loss during mapping due to the high HIV-1 sequence variability and to allow for inter-patient indel variation across the gag-p2/NCp7/p1/p6/pol-PR/RT/IN and env-C2V3-coding regions, sample-specific reference sequences were constructed for each one of these two genomic regions, i.e., positions 1,807 to 5,096 and 6,900 to 7,400, in the HXB2 reference strain (GenBank accession no. K03455), respectively. Mapping of reads from each sample/region occurred in three stages. First, a guide template for mapping was selected from the Los Alamos HIV Sequence Database (http://www.hiv.lanl.gov/content/sequence/HIV/mainpage.html) by comparing 100 randomly selected reads to the corresponding region within all full-length sequences present within the HIV Sequence Database. This comparison was performed using a k-mer approach that rapidly identifies regions of similarity between any two sequences to select a guide sequence for mapping with minimal divergence from the read data, as such divergence is the primary cause of biased data loss. Following the selection of a guide sequence, reads were mapped and aligned using the mapping algorithm previously described. During mapping site indexes in relation to HXB2 were also maintained. Next to reduce diversity between reads and reference, a consensus was generated across each site of the guide sequence and reads re-mapped to this final consensus template. Reads spanning the 3'end of Gag, PR, RT, and INT were then translated and assembled for genotyping.

Variant Caller

Variant calling, the identification and calculation of the frequency of each amino acid present in each genomic position, was calculated using as input a table generated by the Viral Read Mapper, which includes the nucleotide frequencies at each position relative to the reference sequence and with numbering relative to the HIV-1B-HXB2 reference strain. Coverage, indel, codon, and residue frequencies at each position were also listed. Variant Caller summarized the results in a graphical interface with particular focus on sites of known drug resistance based on the latest edition of the IAS-USA HIV Drug Resistance Mutations list. A list of the amino acids at these positions, and their frequencies, was exported as a tabulated text file and used with the HIVdb Program Genotypic Resistance Interpretation Algorithm from the Stanford University HIV Drug Resistance Database (http://hivdb.stanford.edu) to infer the levels of susceptibility to protease, reverse transcriptase, and integrase inhibitors.

In addition, for each dataset, reads spanning amino acid positions (i) 50 to 85 in the protease (HXB2 2,400 to 2,508), (ii) 180 to 215 in the RT (HXB2 3,087 to 3,195), (iii) 130 to 165 in the integrase (HXB2 4,617 to 4,725), and (iv) 1 to 35 in the V3 region (HXB2 7,110 to 7,217) were extracted, truncated and translated for phylogenetic analysis and HIV-1 coreceptor tropism prediction as described below. Within each dataset only one representative of any identical variant was maintained, but the overall frequency stored. All variants with a frequency >1% within the population were aligned using ClustalW and phylogeny reconstructed using the neighbor-joining statistical method as implemented within MEGA 5.05. In this example, minority variants were defined as variation detected at >1% (based on the intrinsic error rate of the system as described below) and 239<20% of the virus population, corresponding to those mutations that cannot be determined using population sequencing.

Genotypic HIV-1 Coreceptor Tropism Determination

HIV-1 co-receptor tropism was predicted from population and deep sequencing V3 sequences using Geno2Pheno. Regarding population V3 sequences, nucleotide mixtures were considered when the second highest peak in the electropherogram was above 25%, and the nucleotide mixtures translated into all possible permutations. Geno2Pheno with a FPR of 2.5% and 5.75% based on optimized cutoffs associated with the analysis of clinical data from MOTIVATE (2.5% and 5.75%) or a FPR of 10% following the recommendations from the European Consensus Group on clinical management of HIV-1 tropism testing as described in the Geno2Pheno website (http://coreceptor.bioinf.mpiinf.mpg.de/index.php), were used for the clinical samples obtained from the Madrid and Seville cohorts, respectively. In the case of deep sequencing V3 sequences, reads spanning amino acid positions 1 to 35 in the V3 region (HXB2 7,110 to 7,217) were extracted and truncated for HIV-1 coreceptor tropism determination using Geno2Pheno with a FPR of 3.5% based on optimized cutoffs for determining HIV-1 coreceptor usage as previously described. Deep sequencing V3 sequences usually spanned 105 nucleotides (35 amino acids), with some minor discrepancies associated with natural HIV-1 variation, which led to V3 sequences with an open reading frame of 96, 99, 102, 108, or 111 nucleotides, all starting and ending with a cysteine codon, i.e., TG(T/C). V3 reads with stop codons (TGA, TAA, or TAG) and/or where the nucleotide length was not a multiple of 3 (e.g., 101, 103, 104, 106, etc.), mostly associated with natural or methodology (PCR or sequencing)-induced insertions and/or deletions, were not included in the analysis. Deep sequencing of the V3 region was considered unsuccessful if reads from the majority variants had to be omitted from the analysis. Finally, plasma samples were classified as containing non-R5 viruses if at least 2% of the individual sequences, as determined by deep sequencing, were predicted to be non-R5.

Statistical Analyses

Descriptive results are expressed as median values, interquartile ranges, standard deviations, and confidence intervals. Pearson's correlation coefficient was used to determine the strength of association between categorical variables. A paired t-test was used to compare the number of drug resistance mutations detected by population and deep sequencing in the same sample. All differences with a P value of <0.05 were considered statistically significant. The kappa coefficient, which assesses a chance-adjusted measure of the agreement between any number of categories, was calculated using ComKappa3 v.3.0.1 to quantify the concordance among the different HIV-1 tropism determinations. All statistical analyses were performed using GraphPad Prism v.6.0b (GraphPad Software, La Jolla, Calif.) unless otherwise specified. gag-2/NCp7/p1/p6/pol-PR/RT/IN and/or env-V3 nucleotide sequences obtained by deep sequencing in this study have been submitted to the Los Alamos National Laboratory HIV-DB Next Generation Sequence Archive.

Results

Characterization of the RT-PCR Amplification Step

As described in Materials and Methods and shown in FIG. 1, the novel HIV-1 genotyping and coreceptor tropism assay requires the RT-PCR amplification of three amplicons covering the HIV-1 gag-p2/NCp7/p1/p6/pol-PR/RT/IN- and env-C2V3-coding regions. The sensitivity of the RT-PCR amplification step was tested by analyzing 79 plasma samples obtained from the ACTU (Cleveland, Ohio). Blood samples from HIV-infected individuals with plasma viral loads ranging from 1,000 to >10,000 copies of viral RNA/ml were used to PCR amplify the C2V3 fragment. Similar to results observed with the two overlapping fragments spanning the gag-p2/NCp7/p1/p6/pol-PR/RT/IN-coding region, RT-PCR products of the correct size were consistently obtained (92%, 73/79) in plasma samples with ≥1,000 copies/ml of HIV RNA (Table 1).

TABLE 1

| Viral load (Copies/ml) | % Positive samples by RT-PCR (No. of positive samples/total No. of samples tested)[a] |
|---|---|
| 1,001-5,000 | 95 (19/20) |
| 5,001-10,000 | 85 (17/20) |
| >10,000 | 95 (37/39) |

[a]RT-PCR amplification of patient-derived env fragments was performed with plasma samples (n = 79) from HIV-infected individuals with viral loads ranging from 1,000 to >10,000 copies of viral RNA/ml as described in Materials and Methods.

Highly reproducible success in RT-PCR amplification of the specific HIV-1 gag-p2/NCp7/p1/p6/pol-PR/RT/IN- and env-C2V3 products was obtained when testing fifteen plasma samples with different viral loads. Details of these tests using two different operators, with different lots of critical reagents, and over a seven-day period, for the gag-p2/NCp7/p1/p6/pol-PR/RT/IN fragments, and for the env-C2V3 fragment. The specificity of the RT-PCR primers and reactions for the env-C2V3 fragment was analyzed using nucleic acids from a series of RNA and DNA viruses (i.e., BKV, CMV, HSV-1, HSV-2, VZV, HBV, HCV, and EBV). As expected, no cross-reactivity was observed with any of these viruses as all RT-PCR reactions failed to generate any detectable amplicons. Similar results were obtained for the gag299/NCp7/p1/p6/pol-PR/RT/IN fragments.

Finally, although most of the HIV-1 genotyping and coreceptor tropism determinations are performed in North America, Europe, and Australia where subtype HIV-1 strains are predominant (http://www.who.int/hiv/pub/global_report2010/en/index.html), it was important to test the ability of the assay to work with more worldwide prevalent non-B HIV-1 variants. For that, the env-C2V3 fragment was RT304PCR amplified from 33 diverse HIV-1 isolates, including five subtype A (HIV-1$_{A\text{-}92RW009}$, HIV-1$_{A\text{-}93RW020}$, HIV-1$_{A\text{-}305\ 92UG029}$, HIV-1$_{A\text{-}V115}$, and HIV-1$_{A\text{-}V120}$), five subtype B (HIV-1$_{B\text{-}92BR014}$, HIV-1$_{B\text{-}92TH593}$, HIV-1$_{B\text{-}US714}$, HIV-1$_{B\text{-}92US727}$, and HIV-1$_{B\text{-}92US076}$), five subtype C (HIV-1$_{C\text{-}92BR025}$, HIV-1$_{C\text{-}C18}$, HIV-1$_{C\text{-}C20}$, HIV-1$_{C\text{-}C21}$, and HIV-1$_{C\text{-}C22}$), six subtype D (HIV-1$_{D\text{-}94UG108}$, HIV-1$_{D\text{-}92UG038}$, HIV-1$_{D\text{-}93UG065}$, HIV-1$_{D\text{-}V89}$, HIV-1$_{D\text{-}V122}$, and HIV-1$_{D\text{-}V126}$), six subtype F (HIV-1$_{F\text{-}93BR029}$, HIV-1$_{F\text{-}93BR020}$, HIV-1$_{F\text{-}VI820}$, HIV-1$_{F\text{-}V164}$, HIV-1$_{F\text{-}CA16}$, and HIV-1$_{F\text{-}CA20}$), two subtype G (HIV-1$_{G\text{-}RU570}$ and HIV-1$_{G\text{-}RU132}$), and four circulating recombinant forms (HIV-1$_{AE\text{-}CMU02}$, HIV-1$_{AE\text{-}CMU06}$, HIV-1$_{AE\text{-}92TH021}$, and HIV-1$_{BF\text{-}93BR029}$). Amplicons of the correct size were obtained for the env-C2V3 (Table 3) and gag-p2/NCp7/p1/p6/pol-PR/RT/IN fragments from all HIV-1 group M isolates analyzed, while negative or inconclusive results were obtained with the HIV-2CBL-20 strain (data not shown).

TABLE 3

| Virus ID[a] | env subtype[b] |
| --- | --- |
| 92RW009 | A |
| 93RW020 | A |
| V115 | A |
| V120 | A |
| 92UG029 | A |
| 92BR014 | B |
| 92TH593 | B |
| 92US714 | B |
| 92US727 | B |
| 92US076 | B |
| C18 | C |
| C20 | C |
| C21 | C |
| C22 | C |
| 92BR025 | C |
| V89 | D |
| V122 | D |
| V126 | D |
| 94UG108 | D |
| 92UG038 | D |
| 92UG065 | D |
| 93BR029 | F |
| VI820 | F |
| V164 | F |
| CA16 | F |
| CA20 | F |
| 93BR020 | F |
| RU570 | G |
| RU132 | G |
| CMU02 | AE |
| CMU06 | AE |
| 92TH021 | AE |
| 93BR019 | BF |

[a]All viruses were obtained from the AIDS Research and Reference Reagent Program (ARRRP), Division of AIDS, NIAID, NIH or as a gift from Dr. Eric J. Arts' laboratory at Case Western Reserve University (CWRU), Cleveland, OH as described in Materials and Methods.
[b]env subtype determined by in---house population (Sanger) sequencing to corroborate published (NIH ARRRP) results.

Estimation of the Intrinsic Error Rate of the Assay

Point mutations, insertions, and deletions (indels) can be introduced in the PCR amplification and sequencing steps of any deep sequencing-based assay. Therefore, it was important to calculate the intrinsic (combined) error rate of our novel HIV-1 genotyping and coreceptor tropism assay since this value could affect the practical limit of detection of the assay. For that, the pNL4-3-hRluc plasmid containing the entire genome of the wild type HIV-1NL4-3 strain was transformed into Electrocomp TOP10 bacteria (Invitrogen). One bacteria colony was grown overnight in 10 ml of bacteria culture, plasmid DNA was purified, and transformed again into bacteria. Ten individual, theoretically identical, bacteria colonies were used for the direct PCR amplification of the gag-p2/NCp7/p1/p6/pol-PR/RT/IN and env-C2V3 fragments (FIG. 2A), and sequenced using the same protocol utilized with the clinical samples. The quality of the DNA sequences was analyzed, and reads filtered, in the Ion Torrent server using a Phred quality score of 20 (Q20), which provides a base call accuracy of 99% (i.e., a 1 in 100 probability of an incorrect base call). The average coverage (sequencing depth) per nucleotide position for the ten clones was 5,750 (range 681 to 15,614) and 3,797 (range 942 to 9,981) for the gag-p2/NCp7/p1/p6/pol-PR/RT/IN and env-V3 regions, respectively (FIG. 2B). For each individual NL4-3 clone, reads were independently mapped to the pNL4-3-hRluc reference sequence and all point mutation and indel information in relation to the reference was analyzed using Segminator II.

Although all ten NL4-3 clones were expected to have no mutations (i.e., point mutation and/or indels) relative to the pNL4-3-hRluc reference sequence, a number of errors were observed throughout the p2/NCp7/p1/p6/pol-PR/RT/IN and V3 regions, ranging from 0% to 29% (mean 0.39%) and 0% to 9.5% (mean 0.37%), respectively (FIG. 2C). The average error frequency due to point mutation was 0.17% (range 0% to 2.5%) and 0.12% (0% to 0.3%) for the p2/NCp7/p1/p6/pol-PR/RT/IN and V3 regions, respectively, whereas the average error rate associated with indels was 0.22% (range 0% to 28%) and 0.25% (0% to 9.2%). Most of the positions with a total (point mutation+indels) error rate above 1% corresponded to the last nucleotide of a homopolymeric region, defined as four or more identical consecutive nucleotides (data not shown). Some of these nucleotide positions corresponded to codons that have been associated with resistance to antiretroviral drugs, e.g., L10 in the protease (3.5%), K101 in the RT (3%), and G193 in the integrase (10.5%) or with coreceptor tropism, e.g., position 11 in the V3 region (2.6%) (FIG. 2D, Table 2). Interestingly, most of the errors in these (homopolymeric) positions corresponded to indels, with a limited number of point mutation errors, e.g., L10 (3.3% vs. 0.22%), K101 (2.7% vs. 0.24%), G193 (9.6% vs. 0.89%), and position 11 in the V3 (2.3% vs. 0.25%), respectively (Table 2). Therefore, considering that (i) the overall error rates for the gag-p2/NCp7/p1/p6/pol-PR/RT/IN and env-V3 regions were 0.39% and 0.37%, respectively, (ii) the point mutation error rates were below 1% for all the codons associated with drug resistance, and (iii) the Variant Caller in the DEEPGEN Software Tool Suite identifies and filters out the indels, it was reasonable to define a frequency of 1% as the minimum threshold to detect mutations in minority HIV-1 variants with this novel assay.

TABLE 2

Error Rate Distribution

| Genomic region[b] | Codon[c] | Sequence[d] | Error Rate[a] (mean ± SD) | | |
|---|---|---|---|---|---|
| | | | Total | Substitutions | Indels |
| Gag/Pol | n.a. | n.a. | 0.0039 ± 0.0001 | 0.0017 ± 0.0001 | 0.0022 ± 0.0001 |
| env-V3 | n.a. | n.a. | 0.0037 ± 0.0002 | 0.0012 ± 0.0001 | 0.0025 ± 0.0002 |
| Protease | L10 | cgacccCTCgtc | 0.0353 ± 0.0086 | 0.0022 ± 0.0002 | 0.0331 ± 0.0051 |
| | M46 | accaaaaATGata | 0.0920 ± 0.0056 | 0.0013 ± 0.0001 | 0.0907 ± 0.0043 |
| | F53 | aggtTTTatc | 0.0436 ± 0.0034 | 0.0021 ± 0.0002 | 0.0415 ± 0.0022 |
| RT | F77 | agaTTCag | 0.0205 ± 0.0028 | 0.0018 ± 0.0001 | 0.0187 ± 0.0011 |
| | K101 | gttaAAAcag | 0.0295 ± 0.0044 | 0.0024 ± 0.0002 | 0.0271 ± 0.0032 |
| | V179 | ataGTCatc | 0.0756 ± 0.0122 | 0.0036 ± 0.0002 | 0.0720 ± 0.0091 |
| | G190 | gtaGGAtct | 0.0221 ± 0.0036 | 0.0012 ± 0.0001 | 0.0209 ± 0.0021 |
| Integrase | G193 | attgggGGGtac | 0.1048 ± 0.0277 | 0.0089 ± 0.0003 | 0.0959 ± 0.0145 |
| V3 | R11 | aagaaaaAGTatc | 0.0256 ± 0.0037 | 0.0025 ± 0.0002 | 0.0231 ± 0.0020 |

[a] Number of combined PCR and sequencing errors, i.e., point mutations, insertions and deletions (indels) per read calculated using Segminator II. Mean and standard deviation (SD) values obtained from 10 independent sequences are indicated.
[b] HIV-1 genomic region analyzed. Gag/Pol and env-V3 correspond to the gag-p2/NCp7/p1/p6/pol-PR/RT/IN and V3 region of the gp120 in the envelope gene, respectively.
[c] Codons associated with resistance to antiretroviral drugs determined to have total error rate values above 1%.
[d] Nucleotide sequence based on the population sequencing of the HIV-1NL4-3 clone, which around these codons was identical to the HIV-1HXB2 reference sequence (GenBank accession number K03455). The respective codon is indicated in uppercase while the nucleotide position associated with the elevated error rate (>1%) is shown in bold and italic. Position numbering is relative to the HIV-1HXB2 reference sequence.

Performance of the Novel Deep Sequencing-Based HIV-1 Genotypic and Coreceptor Tropism Assay The measure of success for any deep sequencing-based assay depends on its ability to generate the maximum number of reads per sequencing run (individual sequences), which then allows the detection of minority variants within the HIV-1 population. This inherent quality is the sum of a series of metrics including, but not limited to, (i) number of samples multiplexed and sequenced per run, (ii) chip loading efficiency, (iii) total number of quality reads, (iv) mean read length, and (v) sequencing coverage at each nucleotide position. Most of the deep sequencing runs described in this study involved multiplexing up to 96 individual samples per sequencing reaction, a number that ensured the minimum coverage of 1,000 per nucleotide position sequenced required to secure the detection of a minor variant present at least at 1% of the population. Efficient loading of ion sphere particles into the Ion 318 chip proved to be user-dependent (mean 72%, range 60% to 84%). The total number of quality reads was proportional to chip loading efficiency (empty wells), with other parameters such as enrichment (no template), polyclonality (ISPs with excess DNA library), test fragments, and primer dimers potentially affecting the final number of total reads in this study (mean 3,827,323; range 3,051,463 to 4,936,375). We used the Ion PGM Sequencing 200 Kit v2 in all sequencing runs, generating an average read length of 147 bp (range, 119 bp to 178 bp). As expected, the average coverage varied with each sequencing run, correlating mostly with the number of multiplexed samples per sequencing reaction, e.g., 20 samples (mean 9,008; range 3,776 to 15,458 and 6,494; range 2,322 to 8,599 in the gag-p2/NCp7/p1/p6/pol-PR/RT/IN and env-V3 region, respectively) or 96 samples (4,485; 1,612 to 7,274 and 1,017; 966 to 1,070).

Figure 7:
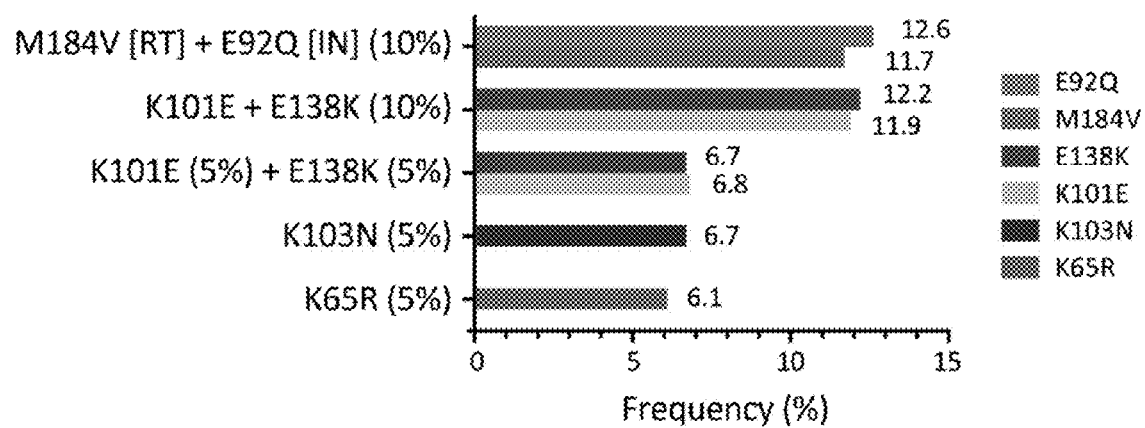
FIG. 7 illustrates a graph showing analytical sensitivity determined in mixtures of plasmid DNA. Five plasmid mixtures containing amino acid substitutions in the HIV-1 pol gene associated with drug resistance, i.e., K65R (5%)+wild type (95%), K103N (5%)+wild type (95%), K101E (5%)+E138K (5%)+wild type (90%), K101E+E138K (10%)+wild type (90%), and M184V (RT)+E92Q (IN) (10%)+wild type (90%) were provided by Gilead Sciences, Inc. (Foster City, Calif.). Plasmid DNA was used as template for the amplification of the gag-p2/NCp7/p1/p6/pol-PR/RT/IN fragment and deep sequenced as described in Materials and Methods. All amino acid changes were detected and quantified at approximately the right proportion.

As described above, we calculated the error rate of the HIV-1 genotyping and coreceptor tropism assay to be below 1% and incorporated this error-defined cutoff into the evaluation of the analytical sensitivity and limit of detection for minority HIV-1 variants. For that, we evaluated extensively the analytical sensitivity of the test to detect and quantify drug resistance mutations (gag-p2/NCp7/p1/p6/pol-PR/RT/IN) and non-R5 variants (env-V3) within mixtures of viral populations. First, we sequenced five plasmid mixtures that contained one or two drug resistance mutations in the RT- and/or IN-coding regions at a frequency of 5% or 10% (i.e., mixture of plasmids containing the respective mutations with a plasmid comprising the wild-type HIV-1HXB2 sequence). As shown in FIG. 7, all mutations were detected and quantified at the expected proportions, including those at a frequency of 5% of the total population. Next, in order to quantify more accurately the analytical sensitivity of the assay, we mixed DNA from a plasmid containing a patient-derived multidrug-resistant gagp2/NCp7/p1/p6/pol-PR/RT/IN fragment in the X4 HIV-1NL4-3 backbone (08-180)(68) with DNA from a plasmid containing the genome of the wild-type HIV-1NL4-3 virus carrying the env gene from the R5 HIV-1YU2 virus. Plasmid DNA was quantified and dilutions used to prepare eight mixtures containing the X4 multidrug-resistant 08-180 plasmid at 0%, 0.1%, 1%, 2%, 3%, 5%, 10%, and 100% at a final concentration of 0.1 ng/ml. This total plasmid concentration (0.1 ng/ml or 100,000 femtograms/ml) theoretically allowed the detection of 100 fg of the plasmid when diluted to 0.1% of the population using nested PCR. Plasmid 08-180pol/NL43-(X4)env was generated by the yeast cloning method, which allows a better representation of the in vivo HIV-1 quasispecies. It contained numerous drug resistance mutations in the protease, RT, and integrase, most of them as majority members of the quasispecies (>99% of the population); however, two amino acid substitutions in the protease were present as minority variants, i.e., L33F at 21.9% and F53Y 1.7%. Interestingly, most drug resistance mutations were detected in the plasmid mixtures containing approximately 1% of the 08-180pol/NL43-(X4) plasmid with the exception of substitution T215Y in the RT, which was identified as 0.95% (FIG. 3A and FIG. 7). As expected, detection of minority mutations leading to two amino acid substitutions (L33F and F53Y) faded quickly and proportional to their frequency in the original population. Similar results were observed during the detection of X4 (NL4-3) V3 sequences, which were detected in a plasmid mixture containing approximately 1% of the 08-180pol/NL43-(X4) env plasmid (FIG. 3A and FIG. 7). Unfortunately, and most likely due to the need to remove V3 sequences with odd open reading frames (as described in Materials and Methods), quantification of X4 sequences in the mixtures containing the 08-180pol/NL43-(X4) env plasmid at 2% and 3% of the population failed or was not accurate, respectively (FIG. 3A and FIG. 7). Finally, in order to mimic the first steps of the assay (i.e., RNA purification and RT-PCR) under controlled conditions, HIV-1-seronegative plasma samples were spiked with two viruses, the first one a patient-derived multidrug-resistant gag-p2/NCp7/p1/p6/pol-PR/RT/IN recombinant virus constructed using the X4 HIV-1NL4-3 backbone (08-194)(68) and a wild-type HIV-1NL4-3 virus carrying the env gene from the R5 HIV-1YU2 virus. Plasma HIV-1 RNA (viral) load was determined (COBAS AmpliPrep/COBAS TaqMan HIV-1 test v2.0, Roche) and dilutions used to prepare four mixtures containing the X4 multidrug-resistant 08-194 virus at 0%, 1%, 5%, and 100% in a final viral load of 100,000 copies/ml. This was the average viral load in plasma samples obtained from highly antiretroviral-experienced patients, usually carrying multidrug-resistant viruses, from recent previous studies in our laboratory. Viral RNA was purified, RT-PCR amplified, barcoded in quadruplicate and deep sequenced as described in Materials and Methods. As expected, all drug resistance mutations from 08-194 were detected when the mixture contained 100% of this virus (FIG. 3B). Interestingly, a few amino acid substitutions were identified by deep sequencing that were not detected in the original study using Sanger sequencing, e.g., F53L (2.2%), V77I (17.4%), I93V (19.7%) in the protease and L100I (3.5%) in the RT coding regions (FIG. 3B). All mutations present at a frequency of >50% in the original 08-194 virus were detected in the 5%:95% (08-194:wild type) mixture; however, none of these mutations were identified when the mixture included 1% of the 08-194 virus (FIG. 3B). Similar results were observed in the env gene, i.e., X4 sequences corresponding to the V3 region of the HIV-1NL4-3 were detected when present at a frequency of 100% and 5% in the viral mixture (FIG. 3B).

Reproducibility of the HIV-1 genotyping and coreceptor tropism assay was evaluated by testing samples from the wild-type HIV-1 control strain (NL4-3), an antiretroviral-naïve (12-596) and two antiretroviral experienced (08-198 and 12-069) individuals. The four samples were RT-PCR amplified in triplicate (3×), each amplicon was barcoded in quadruplicate (4×), DNA libraries prepared in duplicate (2×), and then sequenced twice (2×) for a total of 48 sequences per virus (FIG. 4A). First, reads with a frequency >1 corresponding to 105 bp fragments from the protease, RT, integrase, and V3 regions were used to construct neighbor-joining phylogenetic trees to quantify intra- and inter-patient genetic distances and rule out any potential cross contamination. FIG. 4B shows a clear virus-dependent clustering of sequences in all four HIV-1 regions. As expected, interpatient genetic distances were larger than the range of intra-patient genetic diversity in the four HIV-1 regions, i.e., 0.0495 (0.0023 to 0.0113), 0.0698 (0.0019 to 0.0150), 0.0554 (0.0001 to 0.0145), and 0.36718 (0.0046 to 0.1067) substitutions per site in the protease, RT, integrase, and V3, respectively. Next, the frequency of each nucleotide at each position was compared among the 16 sequences obtained for each one of the triplicate amplicons (n=48) for all four viruses in the gag-p2/NCp7/p1/p6/pol-PR/RT/IN and env-V3 regions. Statistically significant correlations were observed when the three sets of 16 sequences were compared for each virus, with r values ranging from 0.9857 to 0.9996 (P<0.0001, Pearson coefficient correlation) (FIG. 4C). More important, all 48 sequences detected the same amino acids, with similar frequency, in each position in all four viruses. This was evident when only positions associated with drug resistance in the protease, RT, and integrase were evaluated (FIG. 4D). Wild type amino acids were basically the only ones identified in these positions (range, 99.6% to 100%) in the NL4-3 reference virus, while various mutations were detected and different frequencies in the patient-derived samples (FIGS. 4D and 4E). Finally, a series of minor amino acid substitutions were identified repeatedly in the patient-derived samples (08-198, 12-069, and 12-596) at frequencies below the limit of detection of Sanger sequencing, e.g., A98G (3.3%±0.8, mean±standard deviation) and K103N (8.5%±2.6) in virus 12-069 (FIG. 4E).

Comparison of Drug Susceptibility Determination Using Deep Sequencing (DEEPGENHIV) to the Current Standard HIV-1 Genotypic Assays Based on Population Sequencing As described above, a multitude of HIV-1 drug-resistance methods have been developed but only a few have been deployed in the clinical setting, including several genotypic tests based on population sequencing. Here, plasma samples from 166 treatment-experienced HIV-infected individuals from two cohorts of patients (Seville and Madrid) were analyzed using standard population-based HIV-1 genotyping and the novel deep-sequencing assay. The mean CD4+ T-cell count in these patients was 353 cells/µl (interquartile range, IQR: 190-488) and their mean plasma viral load was 69,459 copies/ml (IQR: 5,218-87,000). The length of the antiretroviral treatment varied among individuals, averaging 8.2 years (ranging from 1989 to 2012) and included a diversity of treatment regimens using a multitude of PIs, NRTIs, NNRTIs, raltegravir and/or maraviroc. Altogether a total of 1,701 mutations (379 and 1,322 in the Seville and Madrid cohorts, respectively) in positions associated with drug resistance were detected by both methodologies (i.e., 954 in the protease, 613 in the RT, and 134 in the integrase) (FIG. 5A). As expected, all the drug resistance mutations identified by population sequencing were also detected by deep sequencing, while an additional 1,073 drug resistance mutations (337 and 736 in the Seville and Madrid cohorts, respectively) were detected only by deep sequencing (i.e., 511 in the protease, 1,015 in the RT, and 97 in the integrase) (FIG. 5A). Overall, the difference in the numbers of drug resistance mutations detected by both methods was significant, even when the mutations were quantified by drug class, i.e., an average of 3.1, 2.8, and 0.6 additional mutations associated with PI, RTI, and INI, respectively, were detected by deep sequencing compared to population sequencing (Paired t test, p<0.0001) (FIG. 5A). Interestingly, additional PI (mean 5.3 vs. 3.1) and RTI (3.1 vs. 1.1) but not INI (0.9 vs. 0.8) resistance mutations were identified by deep sequencing in patients from the Seville cohort (FIG. 5A). Unlike some of the HIV-infected individuals from the Madrid cohort, these patients from Seville were not treated with raltegravir. The slight difference in the number of INI mutations detected by deep sequencing in the Seville patients corresponded to the identification of the L101I polymorphism, which has been associated with decreased susceptibility to the INI dolutegravir.

Comparison of HIV-1 Coreceptor Tropism Data Obtained with DEEPGEN HIV to Other Phenotypic or Genotypic HIV-1 Coreceptor Tropism Assays Plasma samples from 114 HIV-infected individuals screened to be treated with a maraviroc-containing regimen, a subset of samples from the same Seville and Madrid cohorts of patients, were analyzed using the novel deep sequencing-based HIV-1 coreceptor tropism assay. These results were compared with a series of genotypic (population sequencing) and phenotypic [ESTA, Trocai, and VERI-TROP] HIV-1 tropism tests. Only samples with results from all the different tests (i.e., 38 and 76 from Seville and Madrid, respectively) were included. Hierarchical clustering analysis grouped the different HIV-1 coreceptor tropism determinations based on their ability to detect R5 and non-R5 (X4, dual tropic, and/or dual mixed, D/M) sequences (FIG. 5B). Plasma samples from the Seville cohort were from patients participating in a study to evaluate the use of an 8-day maraviroc monotherapy clinical test (MCT), the rationale being that plasma viral load in patients carrying non-R5 viruses will fail to decrease at least one log 10, or being undetectable in subjects with <1,000 copies/ml, after receiving maraviroc in this period of time. Overall, in this cohort of patients, the concordance and agreement was high among the different HIV-1 tropism methods, with DEEPGENHIV (Geno2Pheno FPR 3.5%) showing good agreement with population sequencing analyzed using Geno2Pheno/FPR 10% (84.4%, kappa=0.37), MCT (82.9%, kappa=0.44), and ESTA (80%, kappa=0.47) (FIG. 5B). Similar concordance was observed between ESTA and MCT (85%, kappa=0.64) and between population sequencing/Geno2Pheno/FPR 10% and MCT (82.9%, kappa=0.51). Interestingly, a perfect agreement (100%, kappa=1) was observed between MCT and Trocai, the phenotypic HIV-1 tropism assay performed in Seville (data not shown). Using slightly older samples from the Madrid cohort, DEEPGEN™HIV showed excellent agreement with the original Trofile assay (91.7%, kappa=0.79) and good concordance with VERITROP (79.8%, kappa=0.58) or population sequencing/Geno2Pheno/2.5%-5.75% (74.4%, kappa=0.37) (FIG. 5B). Concordance between the original Trofile assay and population sequencing/Geno2Pheno/2.5%-5.75% was comparable (80.3%, kappa=0.54), while a 73.7% (kappa=0.5) agreement was observed between the two phenotypic tests (VERITROP and Trofile) in baseline samples from these patients (FIG. 5B).

Figure 6:
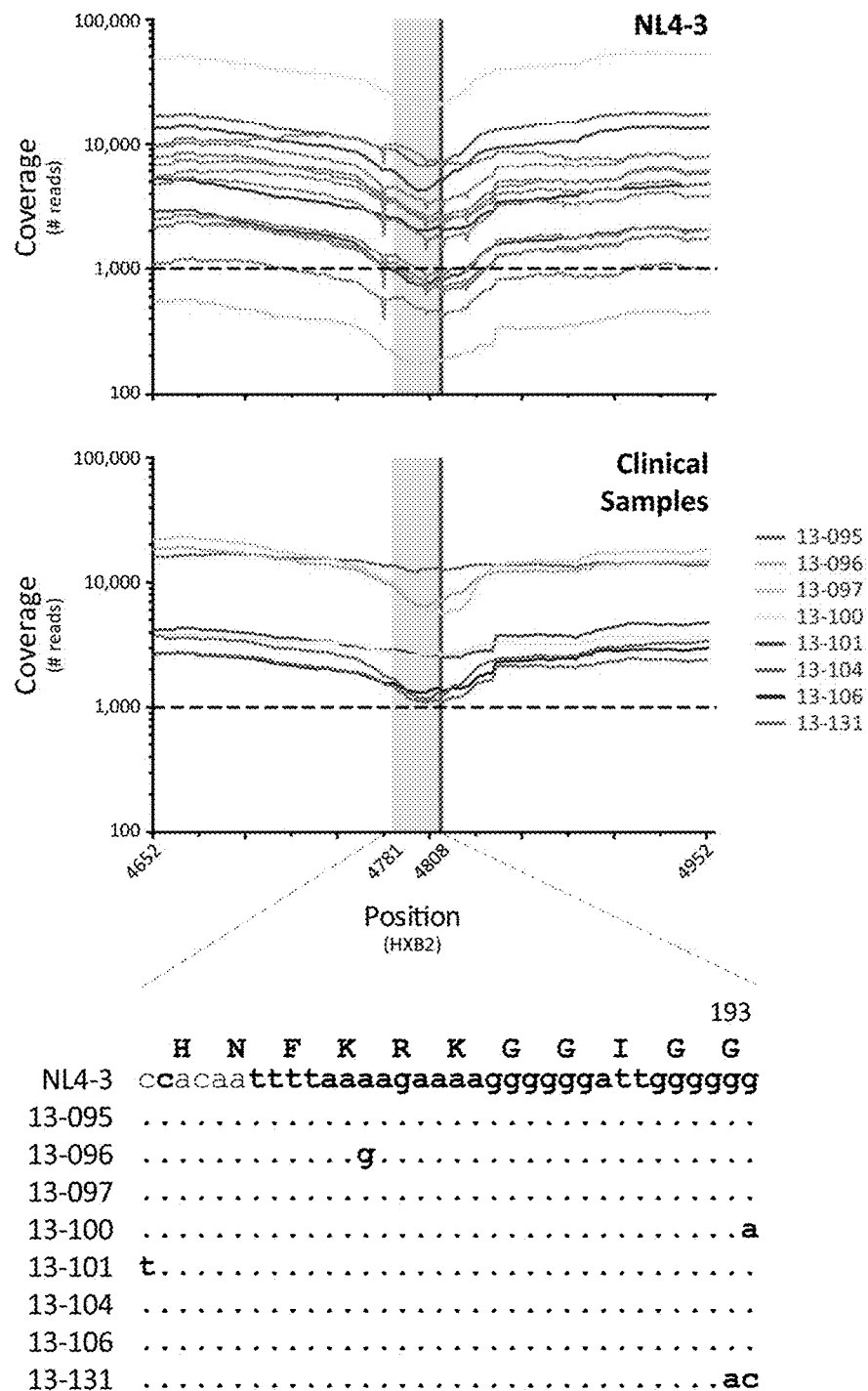
FIG. 6 illustrates plots showing the coverage around codon 193 of the HIV-1 integrase. First panel summarizes the coverage of the 10 HIV-1$_{NL4-3}$ sequences obtained from the clones used to calculate the intrinsic error rate of the assay and 6 HIV-1$_{NL4-3}$ sequences obtained from the positive controls in six regular sequencing runs. The second panel includes the coverage of 8 patient-derived HIV-1 sequences (clinical samples labeled as 13-xxx). The bar indicates the homopolymeric region at and upstream of codon 193, i.e., 25 nucleotides in bold in the nucleotide alignment. The vertical line depicts codon 193.

Any methodology based on PCR amplification and deep sequencing endures the same fundamental problem, that is, errors are introduced during the process. In fact, a limited number of errors are introduced during the PCR step, with most of the errors produced during deep sequencing, mainly insertions and deletions. Thus, here it was important to calculate the intrinsic error rate of the entire system since it would undoubtedly affect the limit of detection of the assay. The combined error rate, i.e., point mutations, insertions, and deletions, of our new HIV-1 genotyping and coreceptor tropism assay was 0.39% and 0.37% for the gag-p2/NCp7/p1/p6/pol-PR/RT/IN and env-V3 regions, respectively. These values were similar to average error rate rates previously reported in the HIV-1 pol or env genes using other deep sequencing platforms, ranging from 0.3% to 0.98%. Approximately a 10-fold higher combined error rate was observed in nucleotide positions associated with homopolymeric regions, resembling findings by other studies describing similar difficulties when sequencing regions with identical consecutive nucleotides. More importantly, some of these homopolymeric regions encompass positions associated with resistance to antiretroviral drugs, which could represent a challenge during the interpretation of minority mutations detected at these positions. Using computational methods we were able to discern between genuine genetic variation and errors introduced during the sequencing process. For example, codon 193 in the integrase showed the highest error rate in the entire HIV-1 genomic region analyzed, i.e., 9.6% indels and 10.5% overall error rate. In HIV-1$_{NL4-3}$ the 25 nucleotides upstream of this position correspond to a series of identical consecutive nucleotides (FIG. 6), which could explain the elevated error rate in this particular region. However, the Ion Torrent software was able to filter most of the reads with sequencing errors, at the expense of reducing approximately 5-fold the coverage around this region (FIG. 2B, FIG. 6) but still above the 1,000 reads required to guarantee the detection of a minor variant present at least at 1% of the population. Moreover, the Variant Caller in the DEEPGEN Software Tool Suite filtered out all the indels at position 193 and, as a consequence, we were able to accurately and repeatedly determine the correct amino acid in all the wild-type HIV-1NL4-3 sequences and the different variants from patient-derived samples (FIG. 6).

Although the forgoing invention has been described in some detail by way of illustration and example for clarity and understanding, it will be readily apparent to one ordinary skill in the art in light of the teachings of this invention that certain variations, changes, modifications and substitution of equivalents may be made thereto without necessarily departing from the spirit and scope of this invention. As a result, the embodiments described herein are subject to various modifications, changes and the like, with the scope of this invention being determined solely by reference to the claims appended hereto. Those of skill in the art will readily recognize a variety of non-critical parameters that could be changed, altered or modified to yield essentially similar results.

The referenced patents, patent applications, and scientific literature, including accession numbers to GenBank database sequences, referred to herein are hereby incorporated by reference in their entirety as if each individual publication, patent or patent application were specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

Having described the invention, we claim:

1. A method for detecting low frequency occurrence of one or more HIV sequence variants associated with drug resistance and HIV tropism, comprising:
   generating a plurality of cDNA species from a plurality of RNA molecules in an HIV sample population,
   clonally amplifying a plurality of first amplicons and second amplicons from the cDNA species, wherein the first amplicons are amplified using first pairs of primers that amplify a HIV genomic region of the cDNA species encoding the Gag proteins p2, p7, p1 and p6, and the protease, reverse transcriptase, and integrase enzymes and the second amplicons are amplified using second pairs of primers that amplify a HIV genomic encoding region of the cDNA species encoding the env-C2V3 region;
   determining the nucleic acid sequence compositions of the clonally amplified first amplicons and second amplicons;
   selecting a guide sequence with minimal divergence from the determined nucleic acid sequence compositions for mapping variants of the determined nucleic acid sequence compositions by comparing the determined nucleic acid sequence compositions to reference sequences;
   identifying variants occurring at least 1% in the determined nucleic acid sequence compositions by comparing the determined nucleic acid sequence compositions to the guide sequence; and
   correlating the determined variants with variants of HIV drug resistance and HIV tropism.

2. The method of claim 1, wherein the first amplicons include first and second overlapping fragments corresponding to the genomic region encoding p2 to 5' region of reverse transcriptase enzyme and the genomic region encoding 3' region of reverse transcriptase enzyme to integrase enzyme.

3. The method of claim 1, wherein the variation associated with HIV tropism is known to be associated with a coreceptor.

4. The method of claim 3, wherein the coreceptor is known to be associated with CCR5 and CXCR4.

5. The method of claim 1, wherein the variation associated with HIV drug resistance is known to be associated with a particular drug class or drug.

6. The method of claim 5, wherein the HIV drug class is selected from the group consisting of protease inhibitors, integrase inhibitors, nucleotide/nucleoside reverse transcriptase inhibitors, non-nucleoside reverse transcriptase inhibitors, and maturation inhibitors.

7. The method of claim 1, wherein the HIV sample population is derived from a single patient.

8. The method of claim 7, wherein the single patient is drug naive.

9. The method of claim 7, wherein the single patient was previously exposed to HIV anti-retroviral drug therapy.

10. The method of claim 1, further comprising administering an HIV drug based on the determined HIV drug resistance and HIV tropism.

11. A method for detecting low frequency occurrence of one or more HIV sequence variants associated with drug resistance and HIV tropism, comprising:
    generating a plurality of cDNA species from a plurality of RNA molecules in an HIV sample population,
    clonally amplifying a plurality of first amplicons and second amplicons from the cDNA species, wherein the first amplicons are amplified using first pairs of primers that amplify a HIV genomic region of the cDNA species encoding the Gag proteins p2, p7, p1 and p6, and the protease, reverse transcriptase, and integrase enzymes and the second amplicons are amplified using second pairs of primers that amplify a HIV genomic encoding region of the cDNA species encoding the env-C2V3 region, wherein the first amplicons include first and second overlapping fragments corresponding to the genomic region encoding p2 to 5' region of reverse transcriptase enzyme and the genomic region encoding 3' region of reverse transcriptase enzyme to integrase enzyme;
    determining the nucleic acid sequence compositions of the clonally amplified first amplicons and second amplicons;
    selecting a guide sequence with minimal divergence from the determined nucleic acid sequence compositions for mapping variants of the determined nucleic acid sequence compositions by comparing the determined nucleic acid sequence compositions to reference sequences;
    identifying variants occurring at least 1% in the determined nucleic acid sequence compositions by comparing the determined nucleic acid sequence compositions to the guide sequence; and
    correlating the determined variants with variants of HIV drug resistance and HIV tropism.

12. The method of claim 11, wherein the variation associated with HIV tropism is known to be associated with a coreceptor.

13. The method of claim 12, wherein the coreceptor is known to be associated with CCR5 and CXCR4.

14. The method of claim 11, wherein the variation associated with HIV drug resistance is known to be associated with a particular drug class or drug.

15. The method of claim 11, wherein the HIV drug class is selected from the group consisting of protease inhibitors, integrase inhibitors, nucleotide/nucleoside reverse transcriptase inhibitors, non-nucleoside reverse transcriptase inhibitors, and maturation inhibitors.

16. The method of claim 11, wherein the HIV sample population is derived from a single patient.

17. The method of claim 16, wherein the single patient is drug naive.

18. The method of claim 16, wherein the single patient was previously exposed to HIV anti-retroviral drug therapy.

19. The method of claim 11, further comprising administering an HIV drug based on the determined HIV drug resistance and HIV tropism.

20. A method of treating HIV in a subject in need thereof, comprising:
  generating a plurality of cDNA species from a plurality of RNA molecules in an HIV sample population obtained from the subject,
  clonally amplifying a plurality of first amplicons and second amplicons from the cDNA species, wherein the first amplicons are amplified using first pairs of primers that amplify a HIV genomic region of the cDNA species encoding the Gag proteins p2, p7, p1 and p6, and the protease, reverse transcriptase, and integrase enzymes and the second amplicons are amplified using second pairs of primers that amplify a HIV genomic encoding region of the cDNA species encoding the env-C2V3 region;
  determining the nucleic acid sequence compositions of the clonally amplified first amplicons and second amplicons;
  selecting a guide sequence with minimal divergence from the determined nucleic acid sequence compositions for mapping variants of the determined nucleic acid sequence compositions by comparing the determined nucleic acid sequence compositions to reference sequences;
  identifying variants occurring at least 1% in the determined nucleic acid sequence compositions by comparing the determined nucleic acid sequence compositions to the guide sequence;
  correlating the determined variants with variants of HIV drug resistance and HIV tropism; and
  administering an HIV drug or combination of HIV drugs based on the determined HIV drug resistance and HIV tropism.

21. The method of claim 1, wherein the method detects both minority drug-resistant viruses and non-R5 HIV-1 variants.

22. The method of claim 11, wherein the method detects both minority drug-resistant viruses and non-R5 HIV-1 variants.

23. The method of claim 20, wherein the method detects both minority drug-resistant viruses and non-R5 HIV-1 variants.

* * * * *